(12) United States Patent
Girouard et al.

(10) Patent No.: US 10,980,469 B2
(45) Date of Patent: Apr. 20, 2021

(54) METHOD AND APPARATUS FOR DETECTING AND CLASSIFYING SEIZURE ACTIVITY

(71) Applicant: Brain Sentinel, Inc., San Antonio, TX (US)

(72) Inventors: Michael R. Girouard, Shavano Park, TX (US); Luke E. Whitmire, San Antonio, TX (US); Jose E. Cavazos, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 272 days.

(21) Appl. No.: 15/766,690

(22) PCT Filed: Oct. 7, 2016

(86) PCT No.: PCT/US2016/055925
§ 371 (c)(1),
(2) Date: Apr. 6, 2018

(87) PCT Pub. No.: WO2017/062728
PCT Pub. Date: Apr. 13, 2017

(65) Prior Publication Data
US 2018/0289310 A1 Oct. 11, 2018

Related U.S. Application Data

(60) Provisional application No. 62/239,161, filed on Oct. 8, 2015.

(51) Int. Cl.
*A61B 5/00* (2006.01)
*A61B 5/0488* (2006.01)

(52) U.S. Cl.
CPC .......... *A61B 5/4094* (2013.01); *A61B 5/0488* (2013.01); *A61B 5/726* (2013.01); *A61B 5/7267* (2013.01); *A61B 5/0015* (2013.01)

(58) Field of Classification Search
CPC ..... A61B 5/7267; A61B 5/726; A61B 5/4094; A61B 5/0488; A61B 5/0015
See application file for complete search history.

(56) References Cited

U.S. PATENT DOCUMENTS 5,349,962 A 9/1994 Lockard et al.
5,810,747 A 9/1998 Brudney et al.
(Continued)

FOREIGN PATENT DOCUMENTS

WO WO2015089455 6/2015

OTHER PUBLICATIONS

Conradsen, et al., "Evaluation of novel algorithm embedded in a wearable sEMG device for seizure detection," 34th Annual International Conference of the IEEE EMBS, San Diego, California, USA, Aug. 28-Sep. 1, 2012, pp. 2048-2051. (4 Pages).
(Continued)

*Primary Examiner* — Christine H Matthews
*Assistant Examiner* — Joshua Daryl D Lannu
(74) *Attorney, Agent, or Firm* — Pizarro Allen PC

(57) ABSTRACT

A method of monitoring a patient for seizure activity may include monitoring the patient by collecting an electromyography signal, determining features of the signal using wavelet analysis and inputting determined feature values into a neural network trained to detect seizure activity. Related apparatuses are also described.

20 Claims, 19 Drawing Sheets

(56) References Cited

U.S. PATENT DOCUMENTS

| | | | |
|---|---|---|---|
| 5,995,868 | A | 11/1999 | Dorfmeister et al. |
| 6,440,067 | B1 | 8/2002 | Deluca et al. |
| 6,549,804 | B1 | 4/2003 | Osorio et al. |
| 7,209,787 | B2 | 4/2007 | DiLorenzo |
| 7,242,984 | B2 | 7/2007 | DiLorenzo |
| 7,558,622 | B2 | 7/2009 | Tran |
| 9,173,609 | B2 | 11/2015 | Nelson |
| 2002/0177882 | A1 | 11/2002 | DiLorenzo |
| 2003/0109905 | A1 | 6/2003 | Mok et al. |
| 2007/0208212 | A1 | 9/2007 | DiLorenzo |
| 2007/0287931 | A1 | 12/2007 | DiLorenzo |
| 2012/0029390 | A1 | 2/2012 | Colborn |
| 2012/0108999 | A1* | 5/2012 | Leininger .......... A61B 5/04015 600/546 |
| 2012/0123232 | A1* | 5/2012 | Najarian ................ G16H 40/67 600/345 |
| 2012/0197092 | A1* | 8/2012 | Luo .......................... A61B 5/11 600/301 |
| 2013/0281797 | A1* | 10/2013 | Sabesan ................ G16H 20/17 600/301 |

OTHER PUBLICATIONS

Conradsen, et al., "Seizure Onset Detection based on a Uni- or Multi-modal Intelligent Seizure Acquisition (UISA/MISA) System," 32nd Annual International Conference of the IEEE EMBS Buenos Aires, Argentina, Aug. 31-Sep. 4, 2010, pp. 3269-3272. (4 Pages).

Conradsen, et al., "Dynamics of muscle activation during tonic-clonic seizures," Epilepsy Research, vol. 104, Issues 1-2, Mar. 2013, pp. 84-93. (10 Pages).

Sandor Beniczky, et al., "Quantitative analysis of surface electromyography during epileptic and nonepileptic convulsive seizures," Epilepsia, vol. 55, Issue 7, Jul. 2014, pp. 1128-1134. (7 Pages).

Rens Wientjes, "Potential Value of Surface Electromyography for Automated Epileptic Seizure Detection for Children in a Home Monitoring System," Eindhoven University of Technology Department of Electrical Engineering Signal Processing Systems, Master of Science Thesis, Project Period May 2006-Aug. 2007, Report 1107, pp. 1-101. (89 Pages).

Conradsen, et al., "Patterns of Muscle Activation During Generalized Tonic and Tonic-Clonic Epileptic Seizures," Wiley Periodicals, Inc., 2011 copyright International League Against Epilepsy, pp. 1-8. (8 Pages).

Conradsen, et al., "Multi-Modal Intelligent Seizure Acquisition (MISA) System—A New Approach Towards Seizure Detection Based on Full Body Motion Measures," 31st Annual International Conference of the IEEE EMBS Minneapolis, Minnesota, USA, Sep. 2-6, 2009, pp. 2591-2595. (5 Pages).

Conradsen et al., "Automatic Multi-modal intelligent seizure acquistion (MISA) system for detection of motor seizures from electromyographic data and motion data," Computer Methods and Programs in Biomedicine 107 (2012) 97-110 (14 Pages).

Muthuswamy et al. "Higher-Order Spectral Analysis of Burst Patterns in EEG" in IEEE Transactions in Biomedical Engineering, vol. 46, No. 1, Jan. 1999. (8 pages).

International Search Report in PCT/US2016/055925, dated Dec. 22, 2016 (2 pages).

Written Opinion in PCT/US2016/055925, dated Dec. 22, 2016 (7 pages).

Yegnanarayana, B "Artificial neural networks for pattern recognition" Sadhana, vol. 19, Part 2, Apr. 1994, pp. 189-238 (50 pages).

Osman A., et al. "Seizure Prediction in Epilepsy and Reaction Diffusion Cellular Nonlinear Networks (RD-CNNs)" Dresdner Sensor-Symposium 2015 pp. 124-125 (2 pages).

Chindemi G., "A Neural Network Study of Predicting Seizures in Epilepsy," Thesis, Univ. of Illinois at Chicago (2012) pp. 1-74 (86 pages.).

Kumar Ajay "Detection of Epileptic Seizure Using Discrete Waelet Transform of EEG Signal" International Journal of Soft Computing and Artificial Intelligence, vol. 3 Issue 1, May 2015 (5 pages).

\* cited by examiner

○⟶ TONIC PHASE OUTPUT NODE
- 0 = ABSENCE OF TONIC PHASE ACTIVITY
- 1 = PRESENCE OF TONIC PHASE ACTIVITY

} FIG. 7A

○⟶ CLONIC PHASE OUTPUT MODE
- 0 = ABSENCE OF CLONIC PHASE ACTIVITY
- 1 = PRESENCE OF CLONIC PHASE ACTIVITY

} FIG. 7B

○⟶ TONIC-CLONIC PHASE OUTPUT NODE
- 0 = ABSENCE OF TONIC-CLONIC PHASE ACTIVITY
- 1 = PRESENCE OF TONIC-CLONIC PHASE ACTIVITY

} FIG. 7C

○⟶ NON EPILEPTIC PSYCHOGENIC SEIZURE OUTPUT NODE
- 0 = ABSENCE OF PSYCHOGENIC ACTIVITY
- 1 = PRESENCE OF PSYCHOGENIC ACTIVITY

} FIG. 7D

○⟶ OXYGEN SATURATION LEVEL
- OUTPUT LEVEL 0-100%

} FIG. 7E

○⟶ DETECTION OF GENERALIZED SEIZURE ACTIVITY
NORMALIZED METRIC OF SIGNAL MAGNITUDE

} FIG. 7F

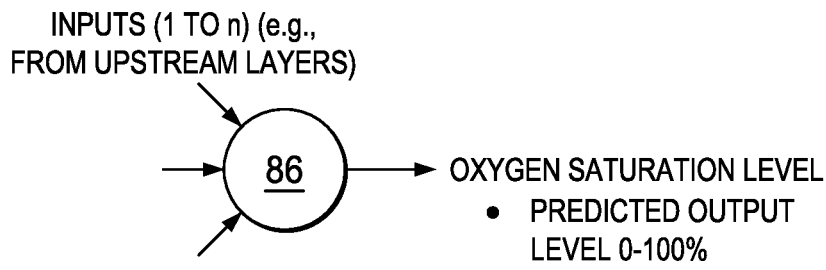
FIG. 9A
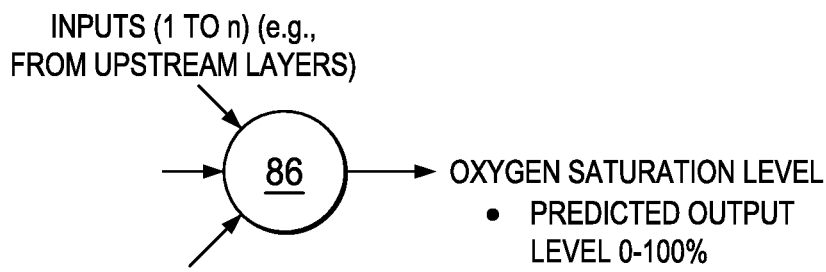
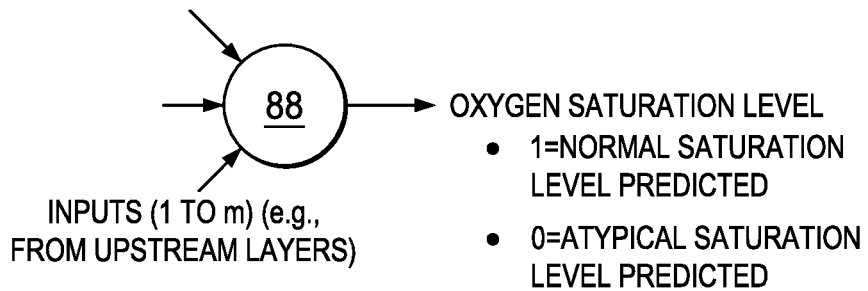
FIG. 9B
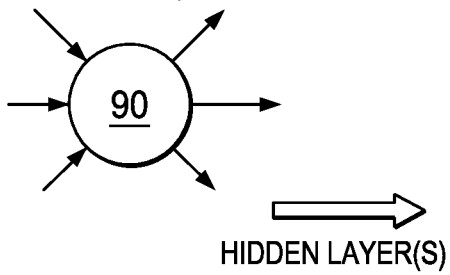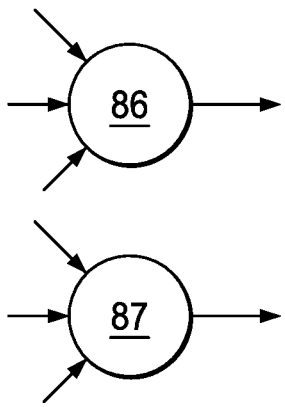
FIG. 9C

BEFORE

TONIC

CLONIC

POST ICTAL

LEVEL 4

METHOD AND APPARATUS FOR DETECTING AND CLASSIFYING SEIZURE ACTIVITY

CROSS-REFERENCE TO RELATED APPLICATION

This application is a U.S. national stage entry of International Application No. PCT/US2016/055925 entitled "METHOD AND APPARATUS FOR DETECTING AND CLASSIFYING SEIZURE ACTIVITY" filed Oct. 7, 2016, which claims priority to U.S. Provisional Patent Application No. 62/239,161 entitled "Method and Apparatus for Detecting and Classifying Seizure Activity" filed Oct. 8, 2015, the disclosures of which are hereby entirely incorporated herein by reference.

COPYRIGHT NOTICE

This application contains material that is subject to copyright protection. Such material may be reproduced exactly as it appears in Patent and Trademark Office patent files or records. The copyright owner otherwise reserves all rights to such material.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system activating different muscles of the body.

Techniques designed for studying and monitoring seizures have typically relied upon electroencephalography (EEG), which characterizes electrical signals using electrodes attached to the scalp or head region of a seizure prone individual or seizure patient. In EEG, electrodes may be positioned so as to measure such activity; that is, electrical activity originating from neuronal tissue. Alternatively, electromyography (EMG) may be used for seizure detection. In EMG, an electrode may be placed on or near the skin, over a muscle, to detect electrical activity resulting from muscle fiber activation.

Detecting signals using EEG typically requires attaching many electrodes and associated wires to the head and using amplifiers to monitor brainwave activity. The multiple EEG electrodes may be very cumbersome and generally require some technical expertise to apply and monitor. Furthermore, confirming a seizure requires observation in an environment provided with video monitors and video recording equipment. Unless used in a staffed clinical environment, such equipment may not be intended to determine if a seizure is in progress, but rather to provide a historical record of the seizure after the incident. Such equipment is usually meant for hospital-like environments where a video camera recording or caregiver's observation may provide corroboration of the seizure, and is typically used as part of a more intensive care regimen such as a hospital stay for patients who experience multiple seizures. Upon discharge from the hospital, a patient may be sent home often with little further monitoring.

Ambulatory devices for diagnosis of seizures are generally EEG-based, but because of the above shortcomings those devices are not designed or suitable for long-term home use or daily wearability. Other seizure alerting systems may operate by detecting motion of the body, usually the extremities. Such systems may generally operate on the assumption that while suffering a seizure, a person will move erratically and violently. For example, motion sensors such as accelerometers may be used to detect violent extremity movements. However, depending upon the type of seizure, this assumption may or may not be true. Electrical signals sent from the brain during some seizures may be transmitted to many muscles simultaneously, which may result in muscles fighting each other and effectively canceling out violent movement. In other words, the muscles may work to make the person rigid rather than cause actual violent movement. Thus, some seizures may not be consistently detected with motion-based sensors such as accelerometer-based detectors.

Ambulatory devices for diagnosis of seizures are generally not suited to grade seizures based on intensity, nor are they suited to differentiate seizure-related signals based on event type. Rather, different types of seizures may often be grouped together. Accordingly, ambulatory devices for seizure detection may be ill-suited to customize responses for different types of detected seizure events. However, not all seizures or seizure-related events may necessarily demand the same response. For example, at least for some patients or some patients in certain situations, seizure events may be detected and the event recorded, but without automatic initiation of a complete and costly emergency response. Thus, other ambulatory devices are not ideally suited for cost-effective monitoring of some patients. Also, using current ambulatory devices, caregivers may mis-diagnose some conditions, including some that may benefit from condition-specific therapies. For example, some events, such as psychogenic or non-epileptic seizure events, may be grouped together with generalized tonic-clonic seizure events. Statistical analysis of event signals may encourage effective diagnosis of some commonly mis-diagnosed conditions. However, other ambulatory detection systems are generally not configured to provide organized statistical information to caregivers as may be used to medically or surgically manage a patient's care.

Accordingly, there is a need for detection methods and apparatuses suitable to identify abnormal brain activity such as may be related to seizure activity and that can be used in non-institutional or institutional environments without many of the cumbersome electrodes to the head or extremities. There is further a need for detection methods that are suited to grade seizures by type and/or intensity and customize alarms so as to provide robust and cost effective patient care. There is also a need for monitoring systems that organize medical data within databases to help medically and surgically manage patient care.

SUMMARY

In some embodiments, a method of monitoring a patient for seizure activity may include monitoring a patient using one or more electromyography electrodes to obtain an electromyography signal; processing with a processor said electromyography signal to determine values of one or more features of said electromyography signal; wherein said processing includes decomposition of the electromyography signal using a wavelet transform; inputting said values of the one or more features of said electromyography signal into a neural network trained to identify seizure activity; processing said values of the one or more features of said electromyography signal using the neural network to determine one or more outputs of the neural network; wherein said one or more outputs indicate the presence of said seizure activity; and initiating a response to detection of said seizure activity.

BRIEF DESCRIPTION OF THE DRAWINGS

FIGS. 7A-7F show embodiments of output nodes of a neural network.

FIGS. 9A-9C show embodiments of parts of a neural network.

DETAILED DESCRIPTION

Figure 1:
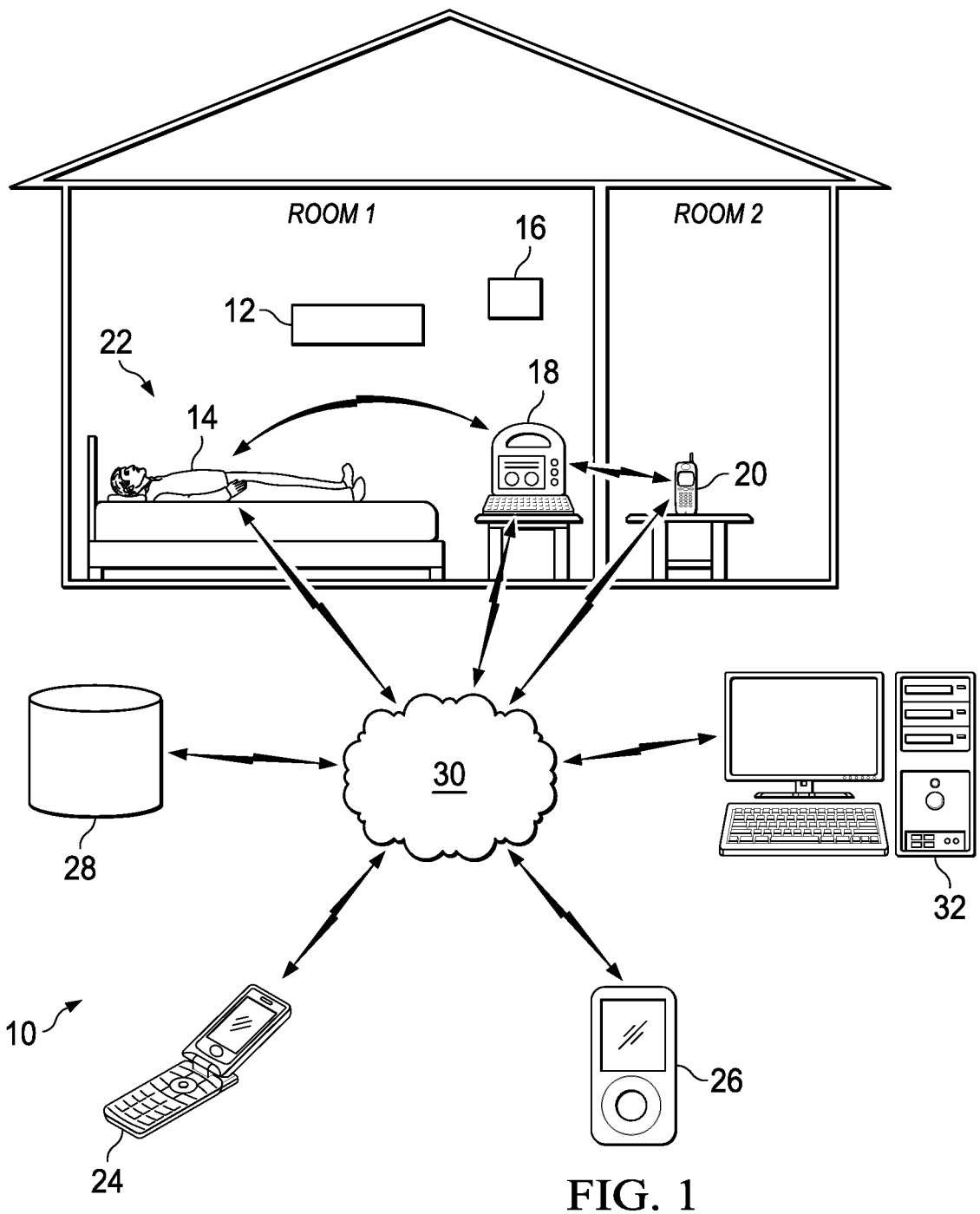
FIG. 1 shows an embodiment of a system for monitoring a patient's motor activity.

The following terms as used herein should be understood to have the indicated meanings.

When an item is introduced by "a" or "an," it should be understood to mean one or more of that item.

Where a range of values is described, it should be understood that intervening values, unless the context clearly dictates otherwise, between the upper and lower limit of that range and any other stated or intervening value in other stated ranges, may be used within embodiments herein.

"Communication" means the transmission of one or more signals from one point to another point. Communication between two objects may be direct, or it may be indirect through one or more intermediate objects. Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), the TCP/IP model, or any other suitable model.

"Comprises" means includes but is not limited to.

"Comprising" means including but not limited to.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

The term "computer program" means a list of instructions that may be executed by a computer to cause the computer to operate in a desired manner.

The term "computer readable medium" means an article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

"Having" means including but not limited to.

"Routine" refers to a method or part of a method that may be used to monitor a patient or may be used to train a neural network. A routine may be run individually in a strategy for monitoring a patient or for training a neural network or may be run in combination with other routine or methods in an overall strategy for monitoring a patient or training a neural network.

"Signal" means a detectable physical phenomenon that is capable of conveying information. A signal may include but is not limited to an electrical signal, an electromagnetic signal, an optical signal, an acoustic signal, or a combination thereof.

The apparatuses and methods described herein may be used to detect seizures and timely alert caregivers of seizure events. The apparatuses may include sensors disposed on, near, or underneath the skin of a patient or attached to a patient's clothing and may be configured for measurement of muscle electrical activity using electromyography. In some embodiments, apparatuses herein may include one or more processors suitable to receive an electromyography signal and process the information to detect electrical signals resulting from muscle activation that may be caused by a seizure. Detection of motor activity using electromyography electrodes is further described in, for example, Applicant's U.S. Pat. Nos. 8,983,591, 9,186,105, 9,439,595, and 9,439,596. Detection of motor activity using electrodes disposed on either or both of the left and the right sides of a patient's body is described in Applicant's U.S. patent application Ser. No. 14/686,475. Detection and qualification of samples of EMG signal including one or more elevations in EMG signal amplitude is described in Applicant's U.S. patent application Ser. No. 14/920,665. The disclosures of all of the aforementioned patents and applications are herein fully incorporated by reference.

In some embodiments, apparatuses and methods herein may include processing a collected EMG signal and/or other sensor data to obtain values of one or more features of the electromyography signal. Features data may then be input into a classification module, which in some preferred embodiments may include a neural network. The neural network may be trained to identify seizure and seizure-related activity.

In some embodiments, processing an EMG signal to generate feature data may include isolating one or more parts of an EMG signal using one or more signal transforms.

In some embodiments, the transform may include a wavelet transform. For example, in some embodiments, a signal may be processed using a Haar wavelet transform, a Daubechies wavelet transform, or other suitable wavelet transform.

In some embodiments, processing of an EMG signal to generate feature data may include processing a collected EMG signal to identify if one or more samples of the EMG signal that include an elevation in signal amplitude are present. Processing may further include determining if the one or more samples meet one or more qualification thresholds suitable to identify that the one or more samples may be indicative of seizure activity.

In some embodiments, feature data may further include other sensor data. For example, included among additional sensors that in some embodiments may be used to generate feature data are ECG sensors, temperature sensors, orientation sensors, position sensors, saturated oxygen sensors, force or pressure sensors, audio sensors, and combinations thereof.

In some embodiments, the systems and methods described herein may be directed to detection of seizure or seizure-related activity. Once seizure or seizure-related activity is detected, an alarm or other appropriate system response may be initiated. For example, responses may include executing any of various alarms. In some embodiments, a response that may be executed based on a detected seizure or seizure-related activity may be tailored based upon characteristics of the detected activity. For example, some responses may include initiation of one or more particular warning or emergency alarm protocols. Characteristics of detected activity, which may be used to determine a response, may, for example, include the type of detected activity, which may include, for example, tonic-clonic, tonic-only, clonic-only, or other types of seizure or seizure-related activity. In some embodiments, detected activity may also be characterized based on an intensity or graded strength of detected activity. In some embodiments, apparatuses and methods herein may further be used to create a searchable log of seizure events to help medically or surgically manage a patient. To facilitate organization of detected seizure or seizure-related events, some events may be automatically classified. For example, automatic classification of seizure events (e.g., based on type and/or graded severity) may be used in the creation of ordered databases including seizure-related data, which is a particularly valuable feature where video corroboration of events is absent or where individual review of sizeable amounts of data by trained professionals, such as medical doctors, would be inconvenient or prohibitively costly.

In some embodiments, the systems and methods described herein may be directed to analysis of patient data and classification of data in ways suitable to help caregivers medically and/or surgically manage patient care. Analysis may be performed either in real-time, such as during physical manifestation of a seizure, or may be executed following collection of patient data. For example, in some embodiments, methods described herein may be used to differentiate epileptic seizures from other events commonly mischaracterized as epileptic seizures, including, for example, non-epileptic psychogenic events. In some embodiments, a neural network or other classification module may analyze sensor data and characterize an event as a generalized tonic-clonic seizure, complex partial seizure, non-epileptic psychogenic seizure, non-seizure movement (or false positive detection), or other event.

The systems described herein may, in some embodiments, include one or more detection units. A detection unit may refer to a device that includes at least one EMG sensor. A detection unit may further include one or more additional sensors. A detection unit may, for example, be woven into a shirt sleeve mounted to an armband or bracelet or otherwise held against a patient's body and attached on or near a muscle of the body, such as by using a support frame around the detection device, elastic band, and/or adhesive material. In some embodiments a sensor may be implanted. A detection unit or EMG sensor may, for example, be attached, coupled, or placed on or near muscles of a patient's arms or legs. By way of nonlimiting example, a detection unit or EMG sensor may, in some embodiments, be placed on or near a patient's biceps, triceps, hamstrings, quadriceps, or other suitable muscle. In some embodiments, attachment of a detection unit or EMG sensor may be made so that the orientation of a detection unit or EMG sensor and an associated muscle is maintained in a known or fixed orientation during monitoring. Accordingly, where the orientation of a detection unit or EMG sensor is known or measured, the orientation of an associated muscle may also be determined.

In some embodiments, a detection unit or EMG sensor may be part of one or more wearable suits or articles of clothing and may include a group of sensors such as sensors on either or both of the left and right sides of a patient's body. A group of detection units or EMG sensors may be placed on a patient such that activity from muscles which typically become activated or abnormally activated during a seizure may be measured. A group of detection units or EMG sensors may be placed on a patient such that signals from both a left side of a patient's body and a right side of a patient's body may be measured. And, in some embodiments, one or more pressure or force sensors may be included together with an EMG sensor on a detection unit. In some embodiments, one or more pressure or force sensors may be positioned so that if a patient is lying on a particular side of his or her body (e.g., as may be typical when a patient is side-sleeping), a detection unit may bear a portion of the patient's weight. Accordingly, an associated force or pressure sensor may detect a force or pressure indicating that a muscle may be at least partially constrained. For example, a pressure or force sensor may be positioned on a portion of a detection unit such as the inner surface of a patient's arm or on some other surface that may be sandwiched between a patient's body and a patient's bed if the patient is side sleeping. A measured force or pressure value may sometimes serve as a feature value that may be input into a neural network. In some embodiments, if a measured force or pressure value is above a force or pressure threshold value, an indication that the threshold was exceeded may be provided to a neural network. For example, if a force or pressure is measured that may indicate that greater than a certain percentage of a patient's weight may be on top of a detection unit, an indication that such a force or pressure was measured may be indicated. Accordingly, in some embodiments, a monitoring system including a neural network may be trained or directed to discount EMG sensor data if the data originated from a muscle that was not free to move during a suspected seizure. Or, data from a muscle that was not free to move during a suspected seizure may be treated differently or weighted differently than if a muscle was free to move. Such data may, for example, improve the accuracy of a neural network or other classification module with which the network or module may identify complex partial seizures or conditions where symmetric or asymmetric muscle activity between the left and right sides of a patient's body may be significant or clinically relevant.

A variety of suitable systems may be used for collecting large amounts of EMG and other patient-related data, organizing such data for system optimization and processing, and for initiating an alarm or other response based on suspected aberrant brain or muscle activity. FIG. 1 illustrates an exemplary embodiment of such a system that may be configured to monitor a patient for seizure or seizure-related activity using the methods described herein. In the embodiment of FIG. 1, a detection system 10 may include a video camera 12, a detection unit 14, an acoustic sensor 16, a base station 18, and an alert transceiver 20. The detection unit 14 may comprise one or more EMG electrodes capable of detecting electrical signals from muscles at or near the skin surface of a patient 22, and delivering those electrical EMG signals to a processor for processing. The EMG electrodes may be attached to the patient 22, and may, in some embodiments, be implanted within the tissue of the patient 22 near a muscle that may be activated during abnormal brain or muscle activity. Implanted devices may, for example, be particularly amenable for some patients where EMG signals may typically be weak such as patients with significant adipose tissue. The base station 18 may comprise a computer capable of receiving and processing EMG signals from the detection unit 14 and/or acoustic data from the acoustic sensor 16, determining from the processed EMG and/or acoustic signals whether a seizure or other abnormal condition may have occurred, and sending an alert to a caregiver. The alert transceiver 20 may be carried by, or placed near, a caregiver to receive and relay alerts transmitted by the base station 18 or transmitted directly from the detection unit 14. Other components that may be included in the system 10, including for example, wireless communication devices 24 and 26, storage database 28, electronic devices for detecting changes in the integrity of an electrode skin interface, and one or more environmental transceivers, are also described in U.S. Pat. No. 8,983,591 and other references incorporated herein.

In using the apparatus of FIG. 1, the patient 22 may, for example, be resting in bed, or may be at some other location as daily living may include, and may have the detection unit 14 in physical contact with or in proximity to his or her body. The detection unit 14 may be a wireless device so that the patient 22 may be able to get up and walk around without having to be tethered to an immobile power source or to a bulkier base station 18. For example, the detection unit 14 may be woven into a shirt sleeve, may be mounted to an armband or bracelet, or may be an implanted device. In other embodiments, one or more detection units 14 may be placed or built into a bed, a chair, an infant car seat, or other suitable clothing, furniture, equipment and accessories used by those susceptible to seizures. The detection unit 14 may comprise a simple sensor, such as an electrode, that may send signals to the base station 18 for processing and analysis, or may comprise a "smart" sensor having some data processing and storage capability. In some embodiments, a simple sensor may be connected via wire or wirelessly to a battery-operated transceiver mounted on a belt or other garment or accessory worn by the patient 22. In some embodiments, a detection system may operate without a base station 18.

The system 10 may monitor the patient 22, for example, while resting, such as during the evening and nighttime hours or during the daytime. If the detection unit 14 on the patient 22 detects a seizure or other abnormal activity, the detection unit 14 may communicate wire or wirelessly, e.g., via a communications network or wireless link, with the base station 18 to a remote cell phone or desktop device via Bluetooth or other signal or simultaneously to a base station 18 and remote cell phone or other device. In some embodiments, a detection unit 14 may send some signals to the base station 18 for further analysis. For example, the detection unit 14 may process and use EMG signals (and optionally or additionally, or in some embodiments ECG, temperature, orientation sensors, saturated oxygen, force or pressure sensor, and/or audio sensor signals) to make an initial assessment regarding the likelihood of occurrence of a seizure, and may send those signals and its assessment to the base station 18 for separate processing and confirmation. If the base station 18 confirms that a seizure or other abnormal activity is likely occurring, then the base station 18 may initiate an alarm for transmission over a network 30 to alert a caregiver by way of email, text, phone call, or any suitable wired or wireless messaging indicator. It should be appreciated that the detection unit 14 may, in some embodiments, be smaller and more compact than the base station 18 and it may be convenient to use a power supply with only limited strength. Therefore, it may be advantageous, in some embodiments, to control the amount of data that is transferred between the detection unit 14 and the base station 18 as this may increase the lifetime of any power supply elements integrated in or associated with the detection unit 14. In some embodiments, if one or more of the detection unit 14, the base station 18, or a caregiver, e.g., a remotely located caregiver monitoring signals provided from the base station 18, determines that a seizure or other condition may be occurring, a video camera 12 may be triggered to collect video information of the patient 22.

In some embodiments, a single sensor may be used to monitor a patient for EMG activity. In other embodiments, at least two sensors may be attached to a patient. In some embodiments, sensors may be configured such that a patient when sleeping may have at least one sensor that is not disposed between a surface of the bed and the patient's body. For example, a patient may have sensors on opposite arms such that if the patient sleeps on either the left or right sides of their body at least one sensor may typically not be disposed against the bed. A monitoring system may, for example, be configured to initiate a response if either or both of muscles on the patient's left or right side are suitably activated to show seizure activity, and in some embodiments, a detected event may be classified based on symmetry or lack of symmetry between the left and rights sides of a patient's body or between various muscle groups.

The base station 18, which may be powered by a typical household power supply and contain a battery for backup, may have more processing, transmission and analysis power available for its operation than the detection unit 14, and may be able to store a greater quantity of signal history and evaluate a received signal against that greater amount of data. The base station 18 may communicate with an alert transceiver 20 located remotely from the base station 18, such as in the bedroom of a family member, or to a wireless or remote device 24, 26 carried by a caregiver or located at a work office or clinic. The base station 18 and/or transceiver 20 may send alerts or messages to caregivers, or medical personnel via any suitable means, such as through the network 30 to one or more of the wireless or remote devices 24, 26 which may, for example be a cell phone, PDA or other client device. The system 10 may thus provide an accurate log of seizures or other patient conditions, which may allow a patient's physician to understand more quickly the success or failure of a treatment regimen. Of course, the base station 18 may simply comprise a computer having an installed program capable of receiving, processing and analyzing signals as described herein, and capable of transmitting an alert. In other embodiments, the system 10 may simply comprise, for example, EMG electrodes and a smartphone, such as an iPhone, configured to receive EMG signals from the electrodes for processing the EMG signals as described herein using an installed program application. In further embodiments, so-called "cloud" computing and storage may be used via network 30 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station 18 or separate transceiver 20. Or the base station 18 may be a smartphone or tablet, for example.

In the embodiment of FIG. 1, the signal data may be sent to a remote database 28 for storage. In some embodiments, signal data may be sent from a plurality of epileptic patients to a remote database 28 or central database and "anonymized" to provide a basis for establishing and refining generalized "baseline" sensitivity levels and signal characteristics of an epileptic seizure or other patient condition. The database 28 and base station 18 may be remotely accessed via network 30 by a remote computer 32 or other computer to allow for updating of detector unit 14 and/or base station 18 software and to allow for data transmission. The base station 18 may generate an audible alarm, as may a remote transceiver 20. All wireless links may be two-way for software and data transmission and message delivery confirmation. The base station 18 may also employ one or all of the messaging methods listed above for notification. The base station 18 and/or detection device 14 may provide an "alert cancel" button to terminate an incident warning.

In some embodiments, a transceiver may additionally be mounted within a unit of furniture or some other structure, e.g., an environmental unit or object. If a detection unit 14 is sufficiently close to that transceiver, such a transceiver may be capable of sending data to a base station 18. Thus, the base station 18 may be aware that a signal or signal of a certain strength or type is being received from that transceiver, and therefore base station 18 may identify the associated environmental unit. In some embodiments, a base station 18 may select specific process settings, e.g., such as including threshold values and other data as described further herein, that is dependent upon whether or not it is receiving a signal from a certain transceiver. Thus, for example, if the base station 18 receives information from a detector and from a transceiver that is associated with a bed or crib, it may treat the data differently than if the data is received from a transceiver associated with another environmental unit, such as, for example, clothing typically worn while an individual may be exercising or an item close to a user's sink where for example a patient may brush his or her teeth. More generally, a monitoring system may, in some embodiments, be configured with one or more elements with global positioning (GPS) capability, and position information may be used to adjust one or more routines that may be used in a detection algorithm. Additionally, time-stamped data associated with a patient's position may be sent to other devices, including, for example, to storage database 28. In some embodiments, data used to train a neural network may be organized based on available position data or data from an environmental sensor. Thus, in some embodiments, a neural network may be trained based on data that is specific for a certain location or activity such as data that is determined while the patient is in bed sleeping.

In some embodiments, components of FIG. 1 may be configured to be minimally intrusive to use while sleeping or minimally interfere in daily activities, may require a minimum of electrodes such as one or two, may require no electrodes to the head, may detect a seizure with motor manifestations or other condition, may alert one or more local and/or remote sites of the presence of a seizure or other medical condition, and may be inexpensive enough for home use.

Figure 2:
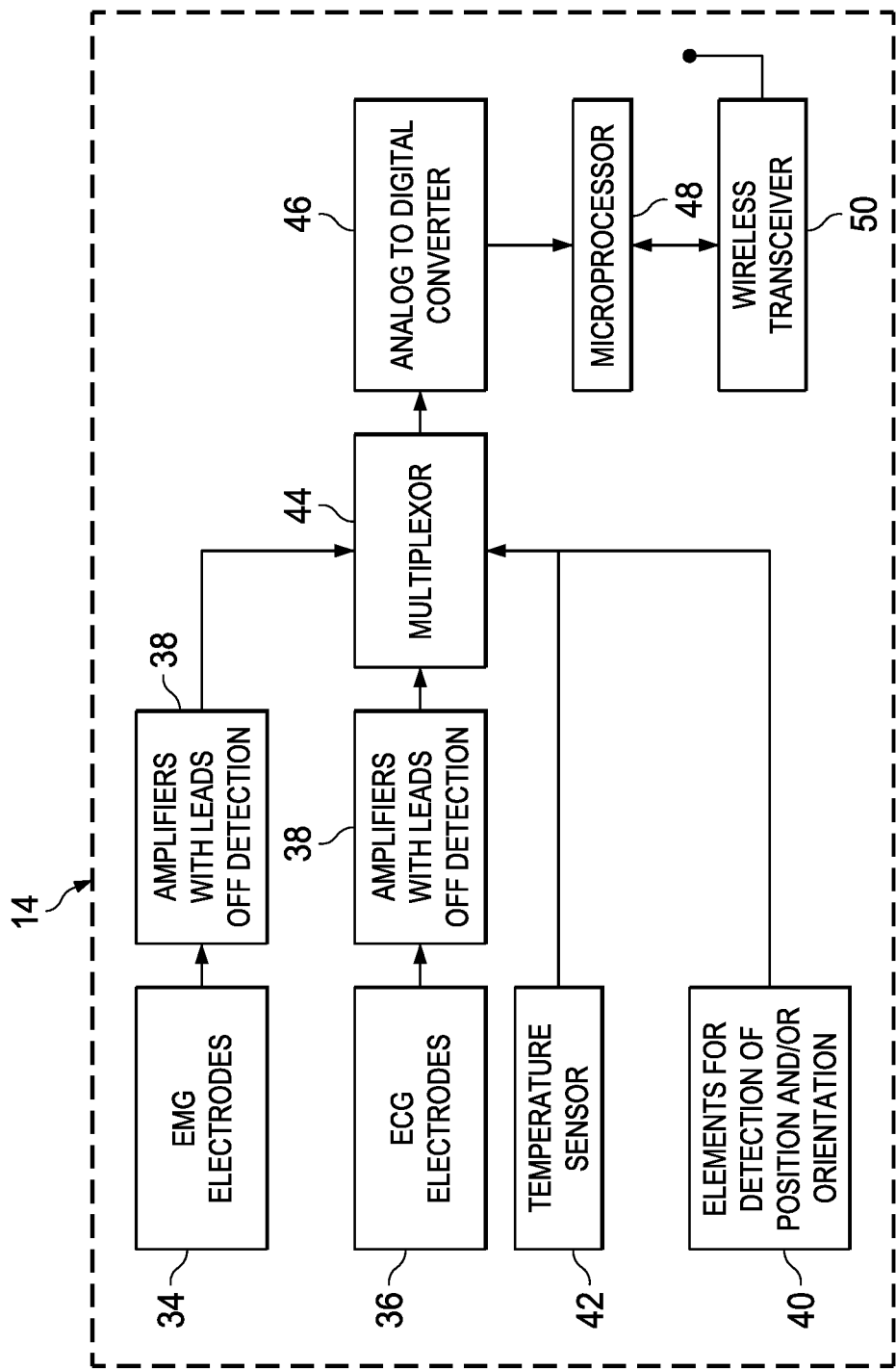
FIG. 2 shows an embodiment of a detection unit.

FIG. 2 illustrates an embodiment of a detection unit 14 or detector. The detection unit 14 may include EMG electrodes 34, and may also include ECG electrodes 36. The detection unit 14 may further include amplifiers with leads-off detectors 38. In some embodiments, one or more leads-off detectors may provide signals that indicate whether the electrodes are in physical contact with the person's body or otherwise too far from the person's body to detect muscle activity, temperature, brain activity or other patient phenomena. In some embodiments, the detection unit 14 may further include one or more elements 40, such as solid state MEMS structures, configured for detection of position and/or orientation of the detection unit 14. For example, an element 40 may include one or more micromachined inertial sensors such as one or more gyroscopes, accelerometers, magnetometers or combinations thereof.

The detection unit 14 may further include a temperature sensor 42 to sense the wearer's temperature. Other sensors (not shown) may be included in the detection unit, as well, such as accelerometers and microphones. Signals from electrodes 34 and 36, temperature sensor 42 and other sensors may be provided to a multiplexor 44. The multiplexor 44 may be part of the detection unit 14 or may be part of the base station 18 if the detection unit 14 is not a smart sensor. The signals may then be communicated from the multiplexor 44 to one or more analog-to-digital (A-D) converters 46. The analog-to-digital converters may be part of the detection unit 14 or may be part of the base station 18. The signals may then be communicated to one or more microprocessors 48 for processing and analysis as disclosed herein. The microprocessors 48 may be part of the detection unit 14 or may be part of the base station 18. The detection unit 14 and/or base station 18 may further include memory of suitable capacity. The microprocessor 48 may communicate signal data and other information using a transceiver 50. Communication by and among the components of the detection unit 14 and/or base station 18 may be via wired or wireless communication.

Of course, the exemplary detection unit of FIG. 2 may be differently configured. Many of the components of the detector of FIG. 2 may be in base station 18 rather than in the detection unit 14. For example, the detection unit may simply comprise an EMG electrode 34 in wireless communication with a base station 18. In such an embodiment, A-D conversion and signal processing may occur at the base station 18. If an ECG electrode 36 is included, then multiplexing may also occur at the base station 18.

In another example, a detection unit 14 may comprise an electrode portion having one or more of the EMG electrode 34, ECG electrode 36, element 40, and temperature sensor 42 in wired or wireless communication with a small belt-worn transceiver portion. The transceiver portion may include a multiplexor 44, an A-D converter 46, microprocessor 48, transceiver 50 and other components, such as memory and I/O devices (e.g., alarm cancel buttons and visual display).

Figure 3:
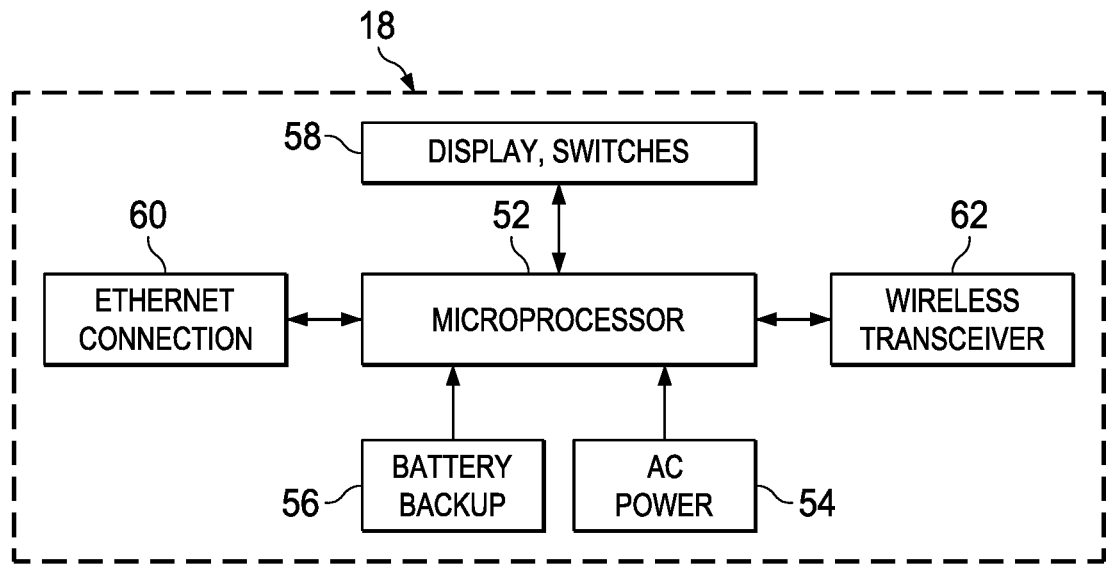
FIG. 3 shows an embodiment of a base station.

FIG. 3 illustrates an embodiment of a base station 18 that may include one or more microprocessors 52, a power source 54, a backup power source 56, one or more I/O devices 58, and various communications means, such as an Ethernet connection 60 and wireless transceiver 62. The base station 18 may have more processing and storage capability than the detection unit 14, and may include a larger electronic display for displaying EMG signal graphs for a caregiver to review EMG signals in real-time as they are received from the detection unit 14 or historical EMG signals from memory. The base station 18 may process EMG signals and other data received from the detection unit 14. If the base station 18 determines that a seizure is likely occurring, it may send an alert to a caregiver via transceiver 50.

Various devices in the apparatus of FIGS. 1-3 may communicate with each other via wired or wireless communication. The system 10 may comprise a client-server or other architecture, and may allow communication via network 30. Of course, the system 10 may comprise more than one server and/or client. In other embodiments, the system 10 may comprise other types of network architecture, such as peer-to-peer architecture, or any combination or hybrid thereof.

Figure 4:
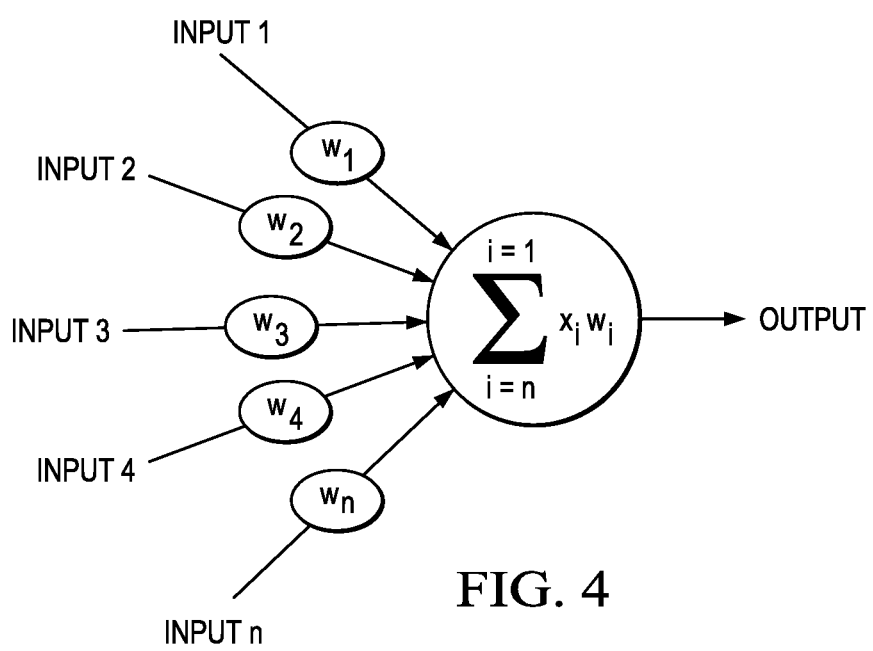
FIG. 4 shows an embodiment of a node of a neural network.

In some embodiments, methods of monitoring a patient for seizure activity may include processing a collected electromyography signal using one or more neural networks. Neural networks may include nodes which may be described in an exemplary manner in reference to FIG. 4. As shown therein, a node of a neural network may be configured to receive data from a number of node inputs ($x_i$). The node inputs ($x_i$) may be weighted and combined. For example, as shown in FIG. 4, in some embodiments, node inputs ($x_i$) may be multiplied by weighting coefficients ($w_i$) and combined in order to determine a node activation value. For example, a node activation value may be calculated as a weighted linear combination of node inputs using Equation 1.

$$a \text{ (activation value)} = \Sigma x_i w_i \ [i=1 \text{ to } i=n] \quad \text{Equation 1}$$

For some nodes or for nodes as applied in some neural networks, an activation value may be compared to a threshold value T which may sometimes be referred to as a bias value. In some embodiments, a comparison may be made between an activation value and a threshold or bias value in order to determine a response or output of a node. For example, an activation value of a node may be compared to a threshold value T, and if the threshold value T is exceeded by the activation value a node output may be selected or determined. For some nodes, a unit node output may be generated if the activation value exceeds its threshold value or bias and a zero node output may be generated if the activation value fails to exceed the threshold value or bias. That is, some node outputs may be described using a function or step-function that may possess either of two possible values. However, in other nodes or other neural networks, a node output may be another function of an activation value. For example, in some embodiments herein, the output of a node may be a sigmoid or other suitable function that depends on the activation value. Accordingly, in some embodiments, an output may be a continuous function that may take any of various values within a certain range.

Figure 5:
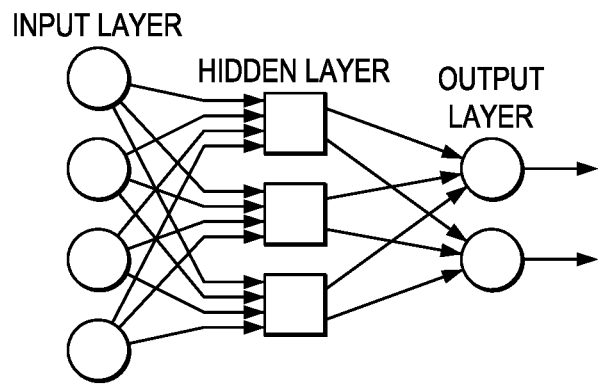
FIG. 5 shows an embodiment of a neural network.

To construct a neural network, individual nodes may be organized in several layers as schematically shown in FIG. 5. An input layer may receive input values, which may be described herein as feature values of a signal, from one or more sources external to the network and feed a processed value of the input values into a next layer of the network. That next layer, which may be a hidden layer, may also feed data into other layers of the network. A hidden layer may generally receive input from the input layer, but may not directly receive external input data or directly output information from the network. For example, as shown in FIG. 5, in some embodiments, a single hidden layer of nodes may be configured between an input layer which receives data from outside of the network, and an output layer which communicates an output response of the network. Some neural networks may be forward feeding networks adopting a configuration in which information generally flows in one direction between the network's layers. However, in some networks described herein, one or more outputs of nodes in one layer may loop back to other nodes in the same or an upstream layer of the network.

In some neural networks described herein, a single hidden layer of nodes may be used. However, in other embodiments, other networks, including some with more than one hidden layer, may be used. In some embodiments, nodes in adjacent layers may be fully interconnected, or fully interconnected during monitoring or in one or more parts of a training routine. For example, all input nodes may be configured to route data to all members of a downstream layer. In other embodiments, different levels of connectivity may be used or learned by a network. For example, in some embodiments, a neural network may be trained using competitive learning, and a trained network may include one or more output nodes that receive input or significant input from only one or several nodes of a network.

In some embodiments, values input into a neural network may include one or more values of features of data extracted from a collected electromyography signal. In some embodiments, one or more values of features derived from additional sensors may be determined and input into a neural network. In some embodiments, a neural network may be configured to receive input feature data and provide output data used to initiate one or more responses in a method of monitoring a patient. For example, in some of those embodiments, a neural network may be directly tasked with initiating one or more alarm responses. In some embodiments, a neural network or part of a neural network may feed one or more of its outputs into one or more data processors that may be tasked with initiating one or more alarm responses. In some of those embodiments, the one or more data processor may also receive other inputs from other sources external to the network and may be tasked with initiating one or more responses. For example, that other processor may receive input from one or more other sensors including, for example, one or more pulse oximeter, ECG sensor, temperature sensor, orientation sensor, saturated oxygen sensor, force or pressure sensor, audio sensor, and/or other sensor.

In some embodiments, a processor may receive and store one or more values from one or more output nodes of a neural network. In some embodiments, a stored data value received from one or more output node of a network may change or adjust over time. For example, in some embodiments, a value output by an output node of a neural network may be transferred to a computer component suitable to store and/or temporarily store and manipulate data such as an accumulation register. An accumulation register may be programmed with a constant, adjustable, and/or varying decay value. That is, a data register may receive a value reflecting the output from a neural network and also adjust a recorded data value at some rate. That rate may be constant or depend on various other conditions, including, for example, the certainty of one or more outputs of a neural network or input features fed into a neural network. Accordingly, in some embodiments, a neural network may provide an output that depends on signals collected over some time period. However, a response may be initiated based on signals collected at times that are different than the aforementioned time period. For example, by adjusting a decay rate of one or more data registers receiving input from a network and initiating a response based on values stored in the one or more data registers, a response may be made more or less dependent on previous signals collected at earlier times in patient monitoring.

A processor receiving inputs from a neural network, which may sometimes be referred to as a supervising or supervisory processor, may further be configured to execute various other tasks. For example, in some embodiments, a supervising processor may receive information from one or more outputs nodes of a network that may be configured to detect a part of a seizure that may sometimes occur as a part in a multi-step seizure pattern. The processor may then, for example, organize data from sources that may detect other parts of a seizure, including, for example, other outputs nodes of a network or other sources external to the network, and the processor may record or report detection of an appropriate multi-step pattern related to seizure activity. In some embodiments, response protocols suitable for detection of a certain seizure pattern may also be organized by a supervising processor. For example, in some embodiments, a supervising processor may receive information about whether a patient is in one of several selectable states, receive information from one or more environmental sensors or other apparatuses capable of providing patient location data, and/or receive other information suitable to direct the processor to initiate one of several selectable transmission or response protocols.

In some embodiments, collection windows processed in one or more feature extraction modules may include windows of different duration widths. Features extracted from the windows may each be fed into a neural network or part of a neural network. Accordingly, in some embodiments, the output of a neural network may depend on and/or be trained to depend on signal data that may be collected over time periods of various durations. Thus, in some embodiments, neural networks may receive inputs from features that carry information over more than one time period. In some embodiments, that flexibility may be used, for example, in configuring a system that may accurately predict and respond to particular signal patterns that operate over more than one time period and do so with a minimal latency or delay period between manifestation of a detected event and alarm initiation. For example, electromyography signals associated with the clonic phase of a seizure may include a series of peaks that generally repeat some number of times during a seizure generally at a rate of about 2 to about 6 times per second. A network may be trained to detect clonic-phase activity by extracting frequency components associated with those peaks based on a collection of electromyography signals and feature extraction using windows of some suitable duration period, such as between about 0.5 seconds to about 2 seconds. In some embodiments, windows for collection of data over that duration or other suitable duration range may be used together with a network trained to detect clonic-phase activity or activity that may be present over one or more parts of clonic-phase activity.

In some embodiments, a neural network may also be trained to detect signals associated with frequency shifts in an electromyography signal during transition between the tonic and clonic phases of a seizure. For example, a training set of data may be encoded with information corresponding to whether a member of training data among the training set of training data or part of the member is affiliated with a transition period between a tonic phase portion and a clonic phase portion of a seizure. In some embodiments, one or more values of features may be extracted from a collected electromyography signal in windows of about 0.2 seconds to about 5 seconds. Those features may be input into a network trained to detect transition periods between a tonic phase and a clonic phase of a seizure.

In some embodiments, a network may be trained to detect electromyography signal patterns that may be indicative of normal recovery from a seizure, abnormal recovery from a seizure, seizure-related patterns different from those associated with epilepsy or combinations thereof. For example, normal seizure recovery may generally include recovery from a seizure with an acceptable pattern of changes in one or more physiological parameters. In some embodiments, identification of abnormal seizure recovery may include detection of patterns of changes in one or more physiological parameters that may be indicative of central nervous system depression. In some embodiments, central nervous system depression may be correlated with low levels of muscle tone, breathing rate, low levels of oxygen saturation, parameters associated with cardiac function, other suitable things and combinations thereof. In some embodiments, to detect and/or train a network to detect the aforementioned patterns, one or more of features may be extracted from a collected electromyography signal in windows of duration suitable to identify changes in clonic-phase burst repetition rate, amplitude regularity, or other trends in burst activity. For example, in some embodiments, features associated with the aforementioned patterns may be isolated from windows that last for up to about 5 seconds or in some cases even longer periods.

In some embodiments, input weights and/or biases of a neural network may be fixed within a monitoring period or between training sessions. However, in some embodiments, one or more input weights and or biases may be dynamically adjusted within a monitoring period. For example, in some embodiments, the output of one or more nodes of a network may be used to adjust weights and or biases of other network nodes. Accordingly, the response of a network at any given point in time may depend upon the weights and/or biases present for the network at that time. Thus, the response of the network may depend on previous signals, including signals that may have been collected at times earlier than a given collection window applied in one or more feature extraction module. In some embodiments, the output of an output node may feed information into one or more node inputs. Thus, in some embodiments, output nodes of a network may be configured to depend on signals that may have been previously collected, such as at times earlier than an input rate of data fed into a network.

In some embodiments, methods herein may include monitoring a patient with a neural network configured to identify atypical brain behavior or changes in brain activity that may initiate atypical motor manifestations. In some embodiments, methods herein may organize and/or prioritize collected electromyography signals to increase the speed and/or accuracy in which a neural network learns to identify motor manifestations associated with atypical brain activity and/or do so for a particular patient. For example, in some embodiments, a method of monitoring a patient may allow for a patient to identify instances of false-detections. For example, as described in U.S. Pat. No. 9,186,105, in some detection systems, if an alarm is triggered, an individual may be given an option to cancel the alarm. The system may then automatically categorize the event as a false positive. In some embodiments, signals collected during a false positive and/or other instances, including, for example, any missed seizures, may be collected and used to retrain a network. In some embodiments, false-detections and or missed detections may be inordinately weighted in training a network to identify patterns of signal collected during those events. In some embodiments, training routines may be configured to train a network to predict how a patient may recover from a seizure. For example, it is anticipated that methods herein including use of neural networks may provide early warning that a patient may be experiencing seizure activity that poses increased risk of central nervous system depression and associated risk that the patient may be at risk of experiencing severe health effects from an identified seizure activity.

Figure 6:
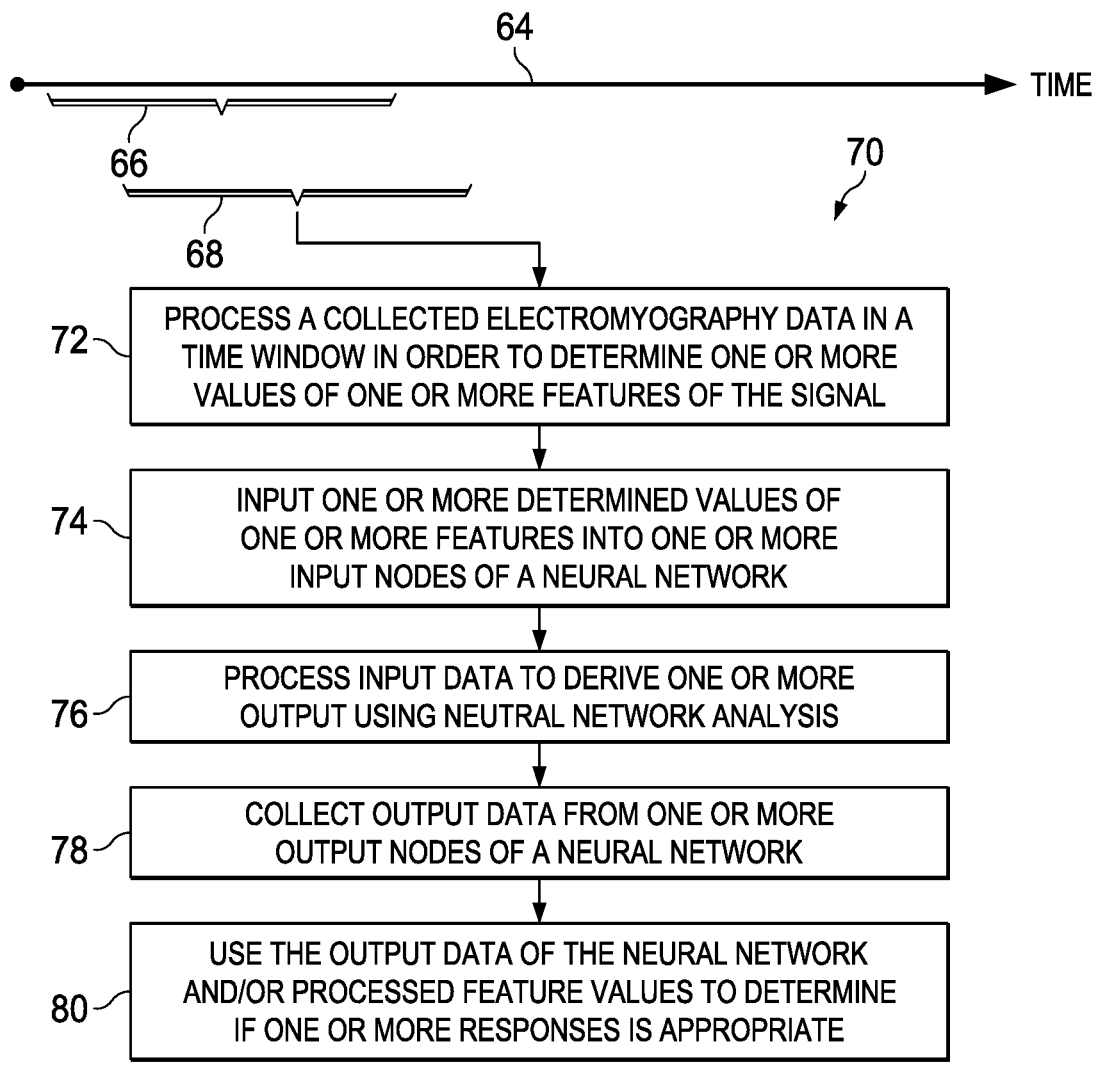
FIG. 6 shows an embodiment of a method of monitoring a patient for seizure activity using a neural network.

FIG. 6 illustrates some embodiments of methods for monitoring a patient for muscle activity resulting from seizure or seizure-related activity. In FIG. 6, a timeline 64 is shown. The timeline 64 represents a monitoring period or session for a patient. During the monitoring session, an electromyography signal and/or other signal information may be collected. In some embodiments, the collected signal may be broken up into a plurality of collection windows. For example, as shown in FIG. 6, during a first collection window 66, electromyography signal may be collected. Likewise, during a second collection window 68, further electromyography signal may be collected. In some embodiments, collection windows may be staggered. For example, some windows may include data from overlapping time periods. However, in other embodiments, collection windows may run consecutively with or without a latency or delay period between them. In some embodiments, as shown in FIG. 6, adjacent or nearby collection windows may have the same duration width. For example, in some embodiments, collection windows may each last for a duration of about 0.2 seconds to about 2 seconds or some other window suitable to extract information suitable for identifying a desired or useful feature of an electromyography signal or other sensor signal. In some embodiments, raw or processed electromyography signal may be directly input into a neural network. The input may, for example, comprise signal collected at the sample rate of one or more EMG electrodes or electrode data may be downsampled and fed into a neural network.

In some embodiments, either or both of the details and/or approximation signals of an electromyography signal processed using wavelet analysis may be used to determine one or more feature values of a signal. In some embodiments, features values fed into a neural network may include one or more amplitude values of the details, approximations or both of a processed signal. In some embodiments, feature values fed into a neural network may include one or more amplitude values of one or more parts of the details, approximations or both of a processed signal. In some embodiments, feature values may be defined from one or more amplitudes of a signal processed using wavelet analysis wherein the one or more amplitudes of signal are selected over a given scale or translation of processed wavelet data.

In some embodiments, as shown in FIG. 6, electromyography signals collected in one or more collection windows during a monitoring session may be sent to one or more processors configured for signal analysis. For example, the one or more processors may be configured to execute one or more of the steps shown for the monitoring routine 70 which may include the steps 72, 74, 76, 78, and 80.

In a step 72, processing of a collected electromyography signal may include determining one or values of one or more features of a collected signal. In some embodiments, features may be obtained from a signal processed using either of a frequency transform or wavelet analysis technique. Wavelet analysis may include continuous wavelet and/or discrete wavelet analysis methods. In some embodiments of wavelet analysis, a signal may be decomposed in levels by passing the signal through a series of filters. For example, in a first level of decomposition, a signal may be passed through each of a high pass filter and a low pass filter resulting in two parts of the original signal. The two filters may generally be related to each other so that the original signal may be substantially reconstructed from the processed signal parts generated at a given level. The now filtered or processed signal parts may be further processed by passing a sampled version of a signal part through a next set of high pass and low pass filters. Decomposition may be repeated several times to generate signal parts at different levels or stages of decomposition. Processed signal from one or more of levels of decomposition may be analyzed and amplitude information of the processed signal identified. For example, the output of low pass filtering may be used to generate processed signal data that is generally referred to as the approximation of the signal. The output of high pass filtering may be used to generate processed signal data that is generally referred to as the details of the signal. In some embodiments, either of the approximations or details of a signal may be processed with an envelope filter and the resulting signal may serve as an input to a neural network.

In the step 74, feature data may be input into one or more nodes of a neural network. In the step 76, input feature data may be processed using the neural network. In some embodiments, the network may be a trained network including weighting coefficients and/or bias coefficients as may be determined using training methods as further described herein. In the step 78, output data from one or more output nodes of a neural network may be collected. As shown in the step 80, output data may be used individually or with other collected data to determine if one or more responses may be deemed appropriate. For example, based on the output data of a neural network and/or other collected data, it may be decided that a patient may be experiencing symptoms of atypical brain activity, including, for example, a seizure, and an alarm may be initiated.

In some embodiments, a neural network described herein may be trained using a set of training data. Training data may include data suitable to determine values of one or more features of a collected signal, including, for example, features that may be extracted from an electromyography signal. Training data may include information suitable to establish one or more conditions affiliated with a patient. For example, a condition of training data may be a known physical condition of the patient at a particular time when electromyography training data was collected. A condition may be associated with a certain part of collected electromyography training data. For example, the presence of a condition may be time stamped with a certain part of a collected electromyography signal. In some embodiments, as described further herein, a condition of training data may be associated with a physical condition experienced by the patient at times following when a part of electromyography training data was collected. Generally, where a condition is affiliated with training data an output node of a neural network may be trained to detect or identify that condition. In this disclosure, a condition, where described in terms of monitoring a patient or where described in terms of a network response with a current set of weighting coefficients and/or biases as may be applied in a stage of training, may sometimes be described as a predicted condition. In contrast, where a patient condition is described by training data that has been subject to external verification and assigned to a desired output of a network, the condition may be described as a known condition. In some embodiments, one or more known conditions affiliated with a patient and which may be associated with training data may be determined using one or more verification methods as further described herein.

In some embodiments, training data may include processed or raw electromyography signal or other signal information collected from a particular patient, all available patients, or from patients of a particular demographic. A patient demographic may, for example, include patients identified by one or more shared or similar characteristics. For example, a patient may be identified by various characteristics including, for example, any combination of age, sex, ethnicity, weight, level of body fat, fat content in the arms, mid-upper arm circumference, fat content in the legs, fitness level or the patient may be defined by other characteristics. A patient's medical history including, for example, history of having seizures, current medications, or other factors may also be considered in defining a patient demographic. In some embodiments, a group of patient's receiving a certain treatment regimen may be assembled together in defining a patient demographic. In some embodiments, a network may be trained in stages. For example, during initial stages of a patient's care, a network may be trained using training data derived from a group of patients, including groups that may or may not include the specific patient to be monitored. In some embodiments, training data used in initial stages of a patient's care may be collected from patients of a certain demographic. In some embodiments, as a patient is monitored throughout a treatment regimen, a network may be trained in one or more stages in which data collected for the patient is used to train or further train a network. In some embodiments, training data may be screened or selected from a larger subset of collected patient data as further described herein.

In some embodiments, training data may include data collected during a dedicated training session. In some embodiments, within one or more dedicated training sessions, an individual may be monitored while engaged in various activities or tasks that model daily activities engaged in by the patient, but may also include other activities specifically tailored to determine a patient's baseline muscle activity level or to determine activity level boundaries or other parameters when muscle activity is initiated in some controlled or defined manner. A dedicated training session may include collection of electromyography data and/or other sensor data while a patient is at rest, executing common daily activities, executing activities which may typically involve vigorous and/or repetitive motion (such as, by way of nonlimiting example, the execution of a maximum voluntary contraction), executing one or more tasks where a patient models a seizure condition, executing one or more tasks where a patient is asked to respond to one or more external factors or any combinations thereof. Activities executed as part of training may be repeated over time at regular or periodic intervals.

In some embodiments, a dedicated training session may include collecting an electromyography signal in a controlled environment. For example, the patient may be monitored in a controlled setting such as in a hospital. A training session may include the collection of signals and/or other information that may be in addition to signals associated with electromyography. For example, additional signals and information may be collected to corroborate, verify, grade, or assign one or more conditions to training data. In some embodiments, a training session may include collecting an electromyography signal and processing the signal in a way to obtain features of the signal that may be different than processing executed during patient monitoring. For example, signals may be analyzed in ways that are computationally rigorous and/or otherwise difficult to apply in real-time by a sensor such as a remote or mobile detection unit. However, to establish or know the condition of a patient during training, those techniques may be useful. For example, in some embodiments, one or more implanted sensors may collect an electromyography signal and may record highly detailed and sensitive patterns associated with muscle atonia. In some embodiments, sensors attached to a patient may monitor muscle activity of the diaphragm or ribcage as may be associated with breathing rates. More generally, in some embodiments, the condition of a patient may be established using one or more external verification methods that may be based on collected and/or processed information that is different from information collected or processed as anticipated in in monitoring. For example, in some embodiments, an external verification method may include use of EEG and video monitoring to assess patient condition information wherein those signals are reviewed after collection by individuals specifically trained to identify characteristics of seizure activity. In some embodiments, during a training session, a patient may be video recorded, monitored with one or more EEG sensors, monitored with one or more sensors configured to determine oxygen levels such as a pulsed oximeter, monitored with one or more ECG sensors, monitored using one or more other sensors, or monitored in other ways and combinations thereof.

In some embodiments, sensor or other data suitable to corroborate, verify, or grade muscle activity, including, for example, activity associated with atypical or typical brain activity, may be used as training data and stored for a patient. For example, electroencephalography data may be recorded and stored to define a baseline pattern of activity associated with a patient during rest or during a seizure. In some embodiments, baseline information about a patient's state of health may include collection of electromyography data while the patient is executing one or more tasks. That data may serve as a baseline measure of the state of the patient at a certain point in time and/or point in time while engaged in a reference activity. For example, a reference activity may include having a patient engage in one or more timed or graded responses to one or more external signals and recording activity using one or more sensors. In some embodiments, baseline sensor data may be recorded at the start of a monitoring regimen or at periodic intervals during times when a patient is being monitored or otherwise treated for a medical condition associated with seizure activity such as epilepsy.

As noted above, in some embodiments, training data may be obtained from electromyography signals collected while monitoring a patient in a controlled setting such as a hospital. However, some embodiments herein are particularly useful in that data collected while monitoring a patient in an ambulatory or home setting may be organized so that the data may, for example, be used in one or more optimization or training protocols. For example, input data suitable to train or continue training a neural network may be collected while a patient is monitored in an ambulatory or home setting. In some embodiments, training data may be derived from data that was originally part of a monitoring session. In some embodiments, methods herein may be configured to correlate patient condition data with electromyography data collected during monitoring. In some embodiments, organized training data may be fed into a network to train or further train the network with some level of screening by a caregiver. In other embodiments, training data may be automatically fed into a network to train or further train the network with limited review or absent direct review by a caregiver.

In some embodiments, methods of training a neural network may include inputting a set of training data into the network and adjusting coefficients of the network such as weighting coefficients and/or biases. For example, a caregiver may feed a set of training data into a neural network, where each member of the set of training data may be related to one or more known or externally established patient conditions. In processing a training data set, one or more members of the set of training data may be input into a network configured with some group of random, initial, or current weights and/or biases. Output data indicating patient conditions predicted by the network when using the group of initial or current weights and/or biases may be generated. A comparison may then be made between the generated output data and known output condition data. In some embodiments, such a comparison may include logging whether one or more particular generated output data points and associated known outputs are in agreement. For example, a log of whether agreement exists between predicted and known conditions may be created. In some embodiments, a comparison may include logging one or more error values associated with a relative degree of agreement between predicted and known outcomes. For example, where an output condition is a continuous function of some parameter of a patient, a difference value or relative difference value may be quantified.

In some embodiments, an algorithm may automatically adjust weights and/or biases of a neural network to search for a best or optimal configuration. For example, an algorithm may search for a configuration that minimizes differences between a generated or predicated output condition and known output condition of the training data. In some embodiments, agreement may be reached when a critical number or rate of training set members agree with a predicted outcome condition. Generally, any of various suitable techniques for adjusting weighting coefficients and/or biases of a network may be used in embodiments herein. In some embodiments, methods based on gradient descent procedures may be used to train a network. In some embodiments, competitive learning may be used to identify one or more inputs or input patterns associated with one or more output nodes. For example, competitive learning may, in some embodiments, be used to identify a single output node (or in some cases a cluster of output nodes) that become configured to respond to a particular input pattern. A cluster of nodes related to a certain input pattern may be weighted to positively contribute towards detection of a certain patient condition. In some embodiments, a cluster of nodes related to a certain input pattern may be weighted to positively contribute towards detection of a certain patient condition, and other nodes in the cluster may negatively contribute towards detection of a certain patient condition.

In some embodiments, weighting coefficients and/or biases of a network may be adjusted so that the network accurately predicts the known output condition for all or some suitable number of members of the input training set. In some embodiments, a summary file describing the results obtained upon executing training or a stage in training may be stored. For example, it may be found that agreement between generated output data and one or more known output conditions is not perfect or that agreement may only be made at some certainty. Various techniques may be used to establish certainty values when using a neural network. For example, various statistical metrics of agreement of fit between generated output data and externally defined condition data may be calculated during a training session. In some embodiments, one or more blind data sets may be input and processed by a network following training or retraining of a network. And, for example, rates of agreement between the blind data set and generated outcomes may be tabulated and used to establish a certainty estimate for the network or for one or more particular output nodes of a network.

In some embodiments, a condition associated with a member of a training data set or part of a member may include the type or phase of seizure experienced by the patient while the training data was collected or other information reflecting a known physical condition of the patient at a time training data was collected. In some embodiments, a condition associated with a member of a training data set or part of a member may include a transition between two parts of seizure. In some embodiments, a condition associated with a member of a training data set or part of member data may include the presence of more than one part of a seizure. In some embodiments, condition data may also be encoded as known to be part of an initial, intermediate, or latter portion of some part of a seizure. In some embodiments, one or more output nodes of a network may be associated with one or more output conditions of a training data set. Generally, where one or more output conditions of a training data set is described in this disclosure, an output node reflecting that condition may be included in a neural network used in patient monitoring. Likewise, in this disclosure, where an output node associated with some condition is described, methods for collection of suitable training data are contemplated.

In the various embodiments herein associated with use of neural networks, output nodes and/or associated training data may be configured in various ways. For example, some output nodes used in some of the embodiments herein are shown in FIGS. 7A-7E. In some embodiments, a network may include an output node associated with the presence or absence of tonic-phase seizure activity as shown in FIG. 7A, clonic-phase seizure activity as shown in FIG. 7B, tonic-clonic seizure activity as shown in FIG. 7C, or non-epileptic psychogenic seizure activity as shown in FIG. 7D. In some embodiments, one or more output nodes may be trained to predict one or more conditions affiliated with a patient and described in a training data set. In some embodiments, an output node may include information for whether a certain condition or patient state such as a type of seizure activity is present. In some embodiments, as also shown in the FIGS. 7A-7D, an output node may output data in the form of a step function. In such a configuration, an output node may, for example, communicate a value of 0 or 1 which may correspond with a prediction for the presence or absence of a certain condition.

In some embodiments, a network may be trained with a training data set, individual members among the data set including a known condition related to a value of a clinically relevant parameter or measurement. For example, a patient condition may be associated with one or more measured values of one or more sensors. In some embodiments, the training data set may include use of sensors that may not be convenient to use in patient monitoring. For example, a sensor used during a training session may be a wired sensor or other sensor that is not comfortable to wear in long term use. Or, a sensor used during a training session may run off a battery that frequently needs to be replaced, and it may not be desirable to use that sensor during a long term care regimen. For example, during a training session a patient may be monitored with electromyography and one or more sensors suitable to measure oxygen saturation levels, which may frequently include a wired connection. In some embodiments, as shown in FIG. 7E, an oxygen saturation level may be an output of a neural network node. As is also evident from FIG. 7E, an output of a node need not be defined using a step function. Rather, in some embodiments, an output may be a function that varies continuously over some range. Any convenient function that is suitable for use in a neural network may be used to model a function that may vary continuously over some range.

In some embodiments, the presence of a seizure at some intensity level or seizure activity of a certain phase at some level of intensity may also be encoded into an output value of an output node of a neural network. For example, some metric of the strength of a seizure or seizure part may be encoded into training data. In some embodiments, a method may communicate to a caregiver the presence of a seizure or seizure activity of a certain phase based on neural network analysis, and an estimate of its intensity or strength may be made by processing collected electromyography signals. For example, to give an intensity value to a detected seizure, the overall power or other metric associated with the amplitude of a collected electromyography signal may be determined. In some embodiments, the overall power or other metric associated with amplitude or magnitude of a collected electromyography signal may be normalized against other values for a patient or patient demographic, and the normalized amplitude value communicated to a caregiver or otherwise incorporated into a decision for how to respond to detected activity.

In some embodiments, data members among a training data set may be associated with one or more conditions that may reflect a patient state that has not yet manifested at a certain time electromyography data was collected. For example, in some embodiments, a patient's oxygen saturation levels may be recorded at various times after manifestation of a seizure and/or after a certain member of a training set or part of training data was collected as described further in relation to FIG. 8.

Figure 8:
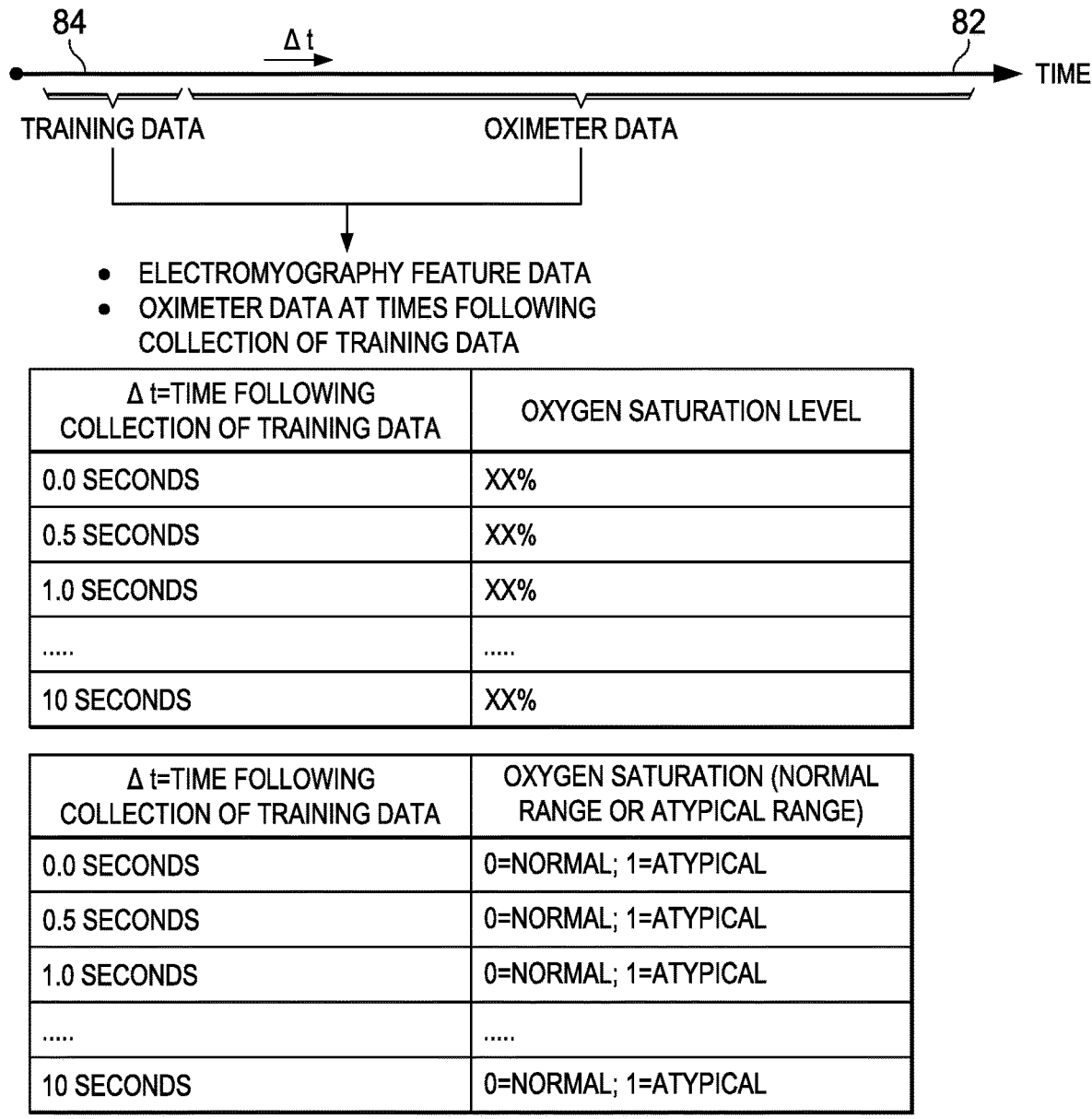
FIG. 8 shows a timeline illustrating collection of training data during a training session.

FIG. 8 schematically represents collection of training data as shown by a collection timeline 82. As shown therein, electromyography training data 84 may be collected at some point in time or over some duration period during a training session. That electromyography training data 84 may be affiliated with information associated with future sensor data. For example, the electromyography training data 84 may be encoded with condition data associated with one or more future sensor measurements from one or more pulse oximeters, cardiac sensors, other sensors, or combinations thereof. As further shown in FIG. 8, oximeter condition data may include the future percentage level of oxygen saturation after some time delay ($\Delta t$) or may include an indication of whether the patient will exhibit oxygen saturation that is within normal or atypical boundaries within some time range in the future. Accordingly, a neural network used in monitoring may be trained to identify aspects of monitoring data that may be indicative of a future oxygen saturation state. For example, in some embodiments, if, following a certain time ($\Delta t$), a saturation level of oxygen drops below 90%, 85%, 80% or some other level deemed by a physician or other caregiver as warranting attention or some response, atypical oxygen saturation may be deemed present. In some embodiments, atypical oxygen saturation levels may be defined against a baseline level typical for a patient or for patients included in a certain patient demographic. Other information may also be collected during a training session and determined to be present or present at some time ($\Delta t$) after a certain electromyography signal is collected. For example, ECG data may be collected for a patient and recorded at times following the collection of an electromyography signal.

In some embodiments, output nodes of a network may be configured to output a predicted future oxygen saturation level, pulse rate or other parameter related to a patient's heart, other predicted future patient parameter or combinations thereof. For example, output nodes of a neural network configured to output a future patient condition are shown in the FIGS. 9A-9C. As shown in FIG. 9A, an output node 86 may output a value of oxygen saturation that may be predicted based on one or more node inputs that depend upon one or more feature values that may be input into a neural network. As shown in the FIG. 9B, in some embodiments, a neural network may include an output node 86 configured to output a predicted percentage oxygen saturation value and an output node 88 may be configured to provide whether a future oxygen saturation level is predicted to be within a normal or atypical range. Similarly, input training data may be encoded with either or both of future measurements of a predicted oxygen saturation level or maximum obtained levels of possible decrease in oxygen saturation and/or encoded with condition values that reflects whether normal or atypical values were exhibited. Other output nodes, including those encoded to provide intermediate gradations of saturation such as may reveal, for example, whether a patent may be expected to exhibit normal, depressed, or severely depressed saturation levels may also be used in some embodiments. Generally, as ($\Delta t$) increases in a training set, the ability of a neural network to predict the behavior may decrease. And, in some embodiments herein, a neural network may output together with a predicted value a certainty estimate of the prediction. An alarm or other suitable response may then, for example, be initiated if a predicted future level of oxygen saturation or other factor that may indicate a patient's level of post-seizure stress is predicted or predicted at some level of certainty.

FIG. 9C shows some embodiments of parts of a neural network including both an output node 86 and input node 90. One or more hidden layers may also typically be included in the network. For example, in some embodiments, a single layer of hidden nodes may be configured downstream of the input node 90 and upstream of the output node 86. Inputs fed into the input node 90 may include one or more feature values derived from a feature process module. Features may depend on collected signals from one or more electromyography or other sensors, and in some embodiments, sensors on both sides of the body may be used to input one or more feature values into a neural network. One example of an output condition that, in some embodiments, may be identified using sensors, including, for example, sensors on both sides of a patient's body, may be the presence or graded intensity of a complex-partial seizure.

In some embodiments, a collected electromyography signal may be processed in one or more feature extraction module. A feature extraction module may, for example, be configured to process electromyography signals and to determine one or more feature values. Feature values may be used individually or in combination to determine inputs applied to an input node of a neural network. In some embodiments, a feature extraction module may be used to process a collected signal so that the form of data derived from the signal is suitable for input into one or more input nodes of a network. For example, in some embodiments, an input node of a neural network may be configured to receive rectified electrode data or electrode data at some expected rate. Accordingly, a feature extraction module may, for example, include components suitable to execute data conversion in hardware and/or software so that an input node of a neural network receives rectified data or data at an expected rate. In some embodiments, one or more analog filters, digital filters, operational amplifiers, processors, electrodes, multiplexors, detection units, base stations, or combinations thereof may be included among components used to execute feature extraction. In some embodiments, features and/or processing steps executed in feature extraction at one or more of a detection unit and a base station may be the same or different. In some embodiments, any of various operations including signal rectification, down sampling, integration, calculation of one or more of a principal component values and/or T-squared component values, analog-to-digital conversion, multiplexing, wavelet analysis, other operations described herein, and combinations thereof may be executed within a feature extraction module.

Figure 10:
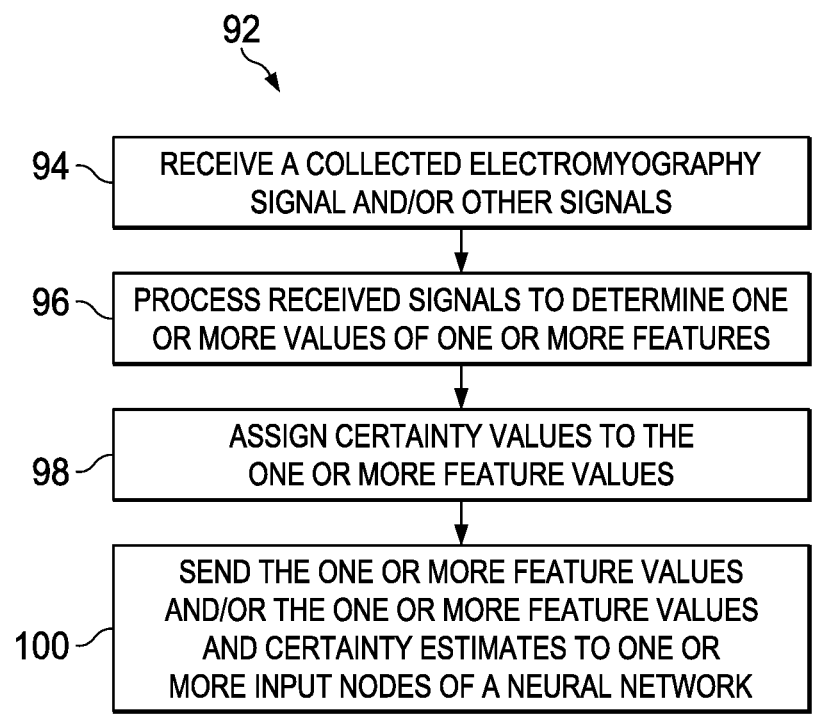
FIG. 10 shows embodiments of operations that may be executed by a feature extraction module.

Some embodiments of operations or steps 92 that may be executed by a feature extraction module are shown in FIG. 10. In the step 94, a feature extraction module may receive an electromyography signal. In the step 96, a feature extraction module may process the received signals to determine one or more values of one or more features of a collected signal. A feature of a collected signal may refer to a general characteristic of the collected signal. In some embodiments, as shown in the step 98, one or more certainty values may be assigned to a feature value. In the step 100, feature values and/or feature values and associated certainty values for the feature value may be sent for processing in a neural network. However, in some embodiments, feature values, including those processed using wavelet analysis, may be processed to determine seizure activity without processing in a neural network.

In some embodiments, methods herein may analyze motor activity for some brain conditions where atypical behavior may be manifested in a more than one way. For example, either or both of relatively high frequency components and/or low frequency components of motor activity may change when a patient exhibits atypical brain activity. Wavelet techniques, as described herein, may be particularly useful as a means to process a signal to identify useful features of the signal that may manifest over different frequencies and/or at different times. For example, by compressing or stretching various wavelets based on a basic or mother wavelet, wavelet transforms may be configured to identify signal features that may manifest at different frequencies and/or times. In some embodiments, one or more wavelet transforms may be used to condition an electromyography signal for processing in a neural network. In some embodiments, a signal may be processed using one or more wavelet transforms. In some embodiments, a signal may be processed using a Haar wavelet transform, a Daubechies wavelet transform, or other suitable wavelet. For example, some wavelet transforms may provide for a more accurate reconstruction of input data than other transforms. However, generally those wavelets may demand somewhat greater processing resources. Selection of one or more wavelet techniques and/or the pairing of those techniques with neural networks of greater or lesser complexity may, in some embodiments, be based on those and/or other considerations as described herein.

In some embodiments, the processing of a collected electromyography signal may include using one or more wavelet transforms. For example, some embodiments herein may include processing of an electromyography signal by converting a raw or lesser processed electromyography signal to another form based on applying a wavelet transformation in which the signal is represented by a group of functions based on one or more mother wavelets. Generally, a mother wavelet may be represented schematically as shown in Equation 2.

$$\int \psi(t)dt = 0 \text{ [Limits } +\infty/-\infty]$$  Equation 2

A group of functions may be generated from a mother wavelet by applying different scaling factors, which may be used to compress or stretch the mother wavelet. Other factors may be used to translate functions over time. For example, as shown schematically in Equation 3, a group or family of functions may be created from a mother wavelet using the factors a and b.

$$\Psi_{a,b}(t) = 1/[a^{1/2}]\psi[(t-b)/a]$$  Equation 3

By varying the factors a and b as shown in Equation 3, a series of functions that may be created as suitable to focus on different frequency components of an electromyography signal.

In some embodiments, wavelets may be constructed by discretely varying factors suitable to translate and compress or stretch a mother wavelet. For example, the factors a and b may be discretized based on Equation 4.

$$a = a_0^m; b = nb_0 a_o^n \text{ [where } m, n \text{ are integers]}$$  Equation 4

In some embodiments, methods herein may include use of a group or family of wavelets wherein the wavelets include orthogonal wavelets generated according to principles originally based on work by Ingrid Daubechies. That is, in some embodiments herein, a discrete wavelet transform procedure may be used to process an electromyography signal based on the construction of Daubechies wavelets.

Figure 11A:
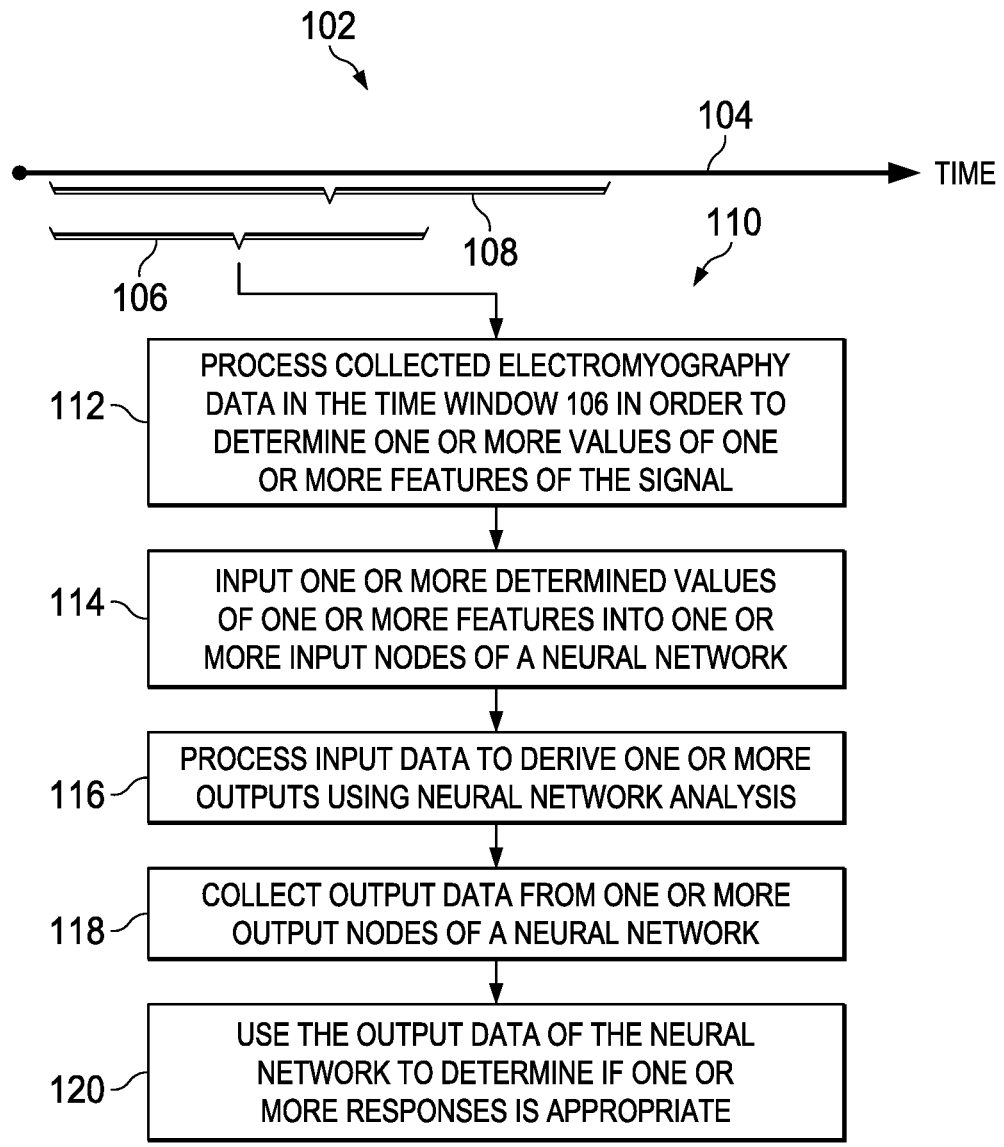
FIGS. 11A-11B show additional embodiments of methods of monitoring a patient for seizure activity using a neural network.
Figure 11B:
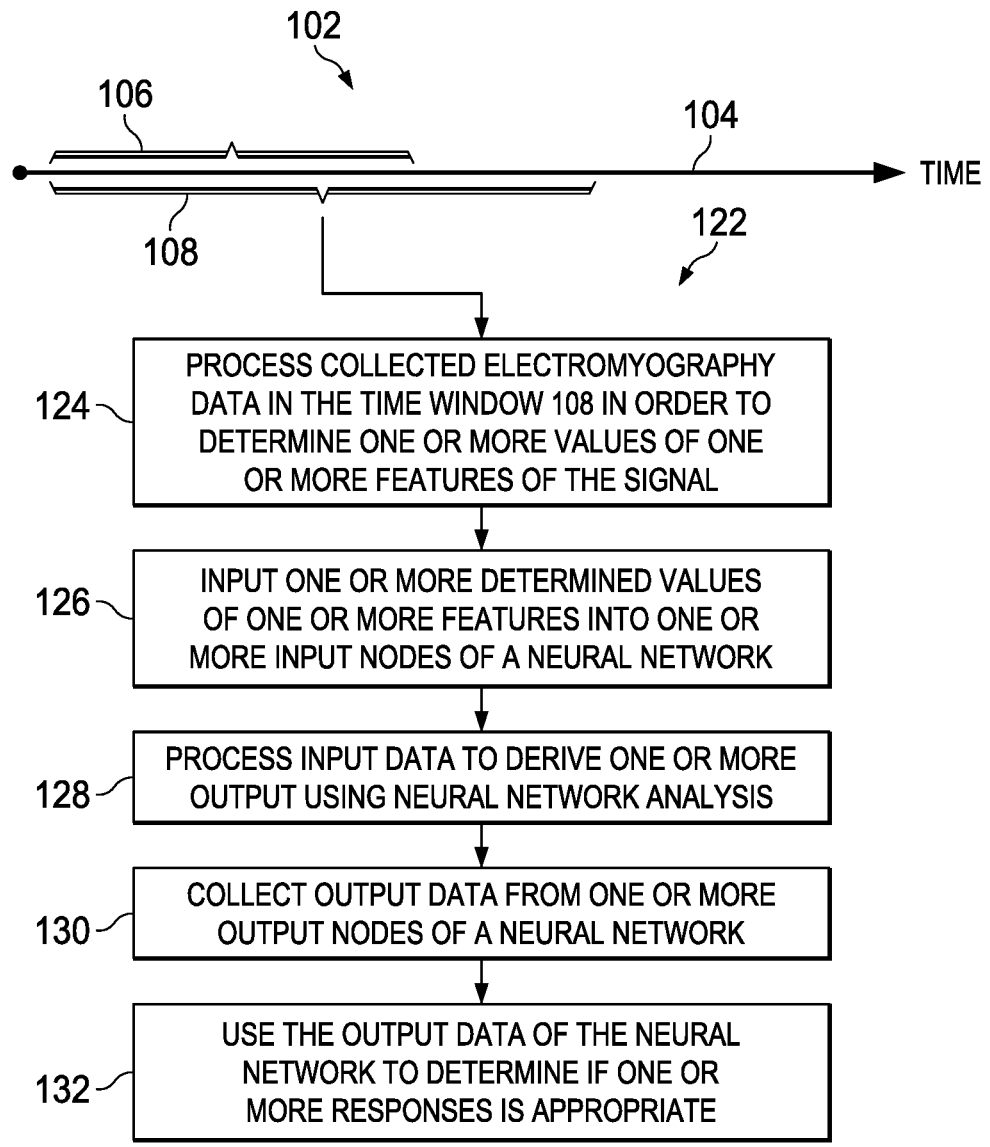

FIGS. 11A and 11B illustrate some embodiments of a method 102 for monitoring a patient for seizure activity. In the method 102, an electromyography signal may be collected. For example, as shown in FIG. 11A, electromyography signals may be collected during times represented by the timeline 104. As shown therein, the collection period may be broken up into various collection windows including, for example, a first time window 106 and a second time window 108. In some embodiments of the method 102, the first time window 106 and the second time window 104 may be of different duration widths.

Signals collected in the first time window may be processed using the routine 110 which may include the steps 112, 114, 116, 118, and 120. In the step 112, processing an electromyography signal collected in the first time window may include determining one or values of one or more features of the collected signal.

In the step 114, feature data may be input into one or more input nodes of a neural network. In the step 116, input feature data may be processed using the neural network. In some embodiments, the network may be a trained network including weighted coefficients and/or bias coefficients as may be determined using training methods as further described herein. In the step 118, output data from one or more output nodes of a neural network may be collected. As shown in the step 120, output data may be used individually or with other collected data to determine if one or more responses may be deemed appropriate and/or initiated.

As shown in FIG. 11B, signals collected in the second time window may be processed using the routine 122 which may include the steps 124, 126, 128, 130, and 132. In the step 124, processing of an electromyography signal collected in the second time window 108 may include determining one or values of one or more features of the collected signal.

In the step 126, feature data may be input into one or more input nodes of a neural network. In the step 128, input feature data may be processed using the neural network. In some embodiments, the network may be a trained network including weighted coefficients and/or bias coefficients as may be determined using training methods as further described herein. In the step 130, output data from one or more output nodes of a neural network may be collected. As shown in the step 132, output data may be used individually or with other collected data to determine if one or more responses may be deemed appropriate and/or initiated.

In some embodiments, feature extraction as executed in the steps 112, 124 may include processing of signals over different collection periods. For example, the first window 106 may be of shorter duration than the second time window 108. In some embodiments, various criteria may be considered in determining a duration width of one or more of the windows 106, 108.

In some embodiments, for example, time windows described herein may be long enough so as to capture or bound one or more descriptive features or aspects of a seizure. For example, included among descriptive features of a seizure described herein are clonic-phase bursts. Clonic-phase bursts are described in a number of applications commonly owned by Applicant including U.S. Pat. No. 8,983,591 issued Mar. 17, 2015. Elevated portions of clonic-phase bursts may generally last for a period of about 50 milliseconds to about 400 milliseconds. An adjacent period of reduced intensity may also be present on either side of elevated portions of clonic-phase bursts. Clonic-phase bursts may generally repeat at least several times during a seizure and may be present about 2 to about 6 times per second. At least over some periods of the clonic phase of a seizure, the average rate of presentation of clonic-phase bursts may be about the same; that is, several fairly uniform clonic-phase bursts may tend to manifest together in a time period. In some embodiments, to collect information about a burst pattern descriptive feature of seizure activity, electromyography signals may be collected over time periods of between about 0.5 second to about 2 seconds. In some embodiments herein, this descriptive feature may be well detected using detail information provided by a wavelet transform. In some embodiments, feature extraction may include collection of detail information of a signal at one or more levels of signal decomposition. For example, in some embodiments, first collection window 106 of method 102 may last for a duration of up to about 2 seconds or about 0.5 second to about 2 seconds, and within the collection window 106 the magnitude of one or more parts of the details of a decomposition signal at one or more levels, including, for example, a third level, fourth level, or fifth level of signal decomposition, may be fed into a neural network trained to identify seizure or clonic-phase seizure activity.

The condition that nearby clonic-phase bursts of similar form may generally be present may sometimes break down as a patient recovers from a seizure. For example, burst rate may generally decrease during normal seizure recovery. For example, an adjacent period of electromyography signal next to an elevated portion of a clonic-phase burst may generally increase during later stages of the clonic phase of a seizure. Other changes in burst amplitude may also hold diagnostic value. In some embodiments, to collect information about changes in a burst pattern, electromyography signals may be collected over time periods of between about 1 second to about 10 seconds. In some embodiments, feature extraction may include collection of detail and/or approximation information of a signal at one or more levels of signal decomposition. For example, in some embodiments, second collection window 108 of method 102 may last for a time of about 1 second to about 10 seconds, and within the collection window 108 the magnitude of one or more parts of the details of a decomposition signal at one or more levels, including, for example, a third or fourth level of signal decomposition, may be fed into a neural network trained to identify seizure or clonic-phase seizure activity. Approximation data from one or more levels may also be fed into an input node of a neural network.

Figure 12:
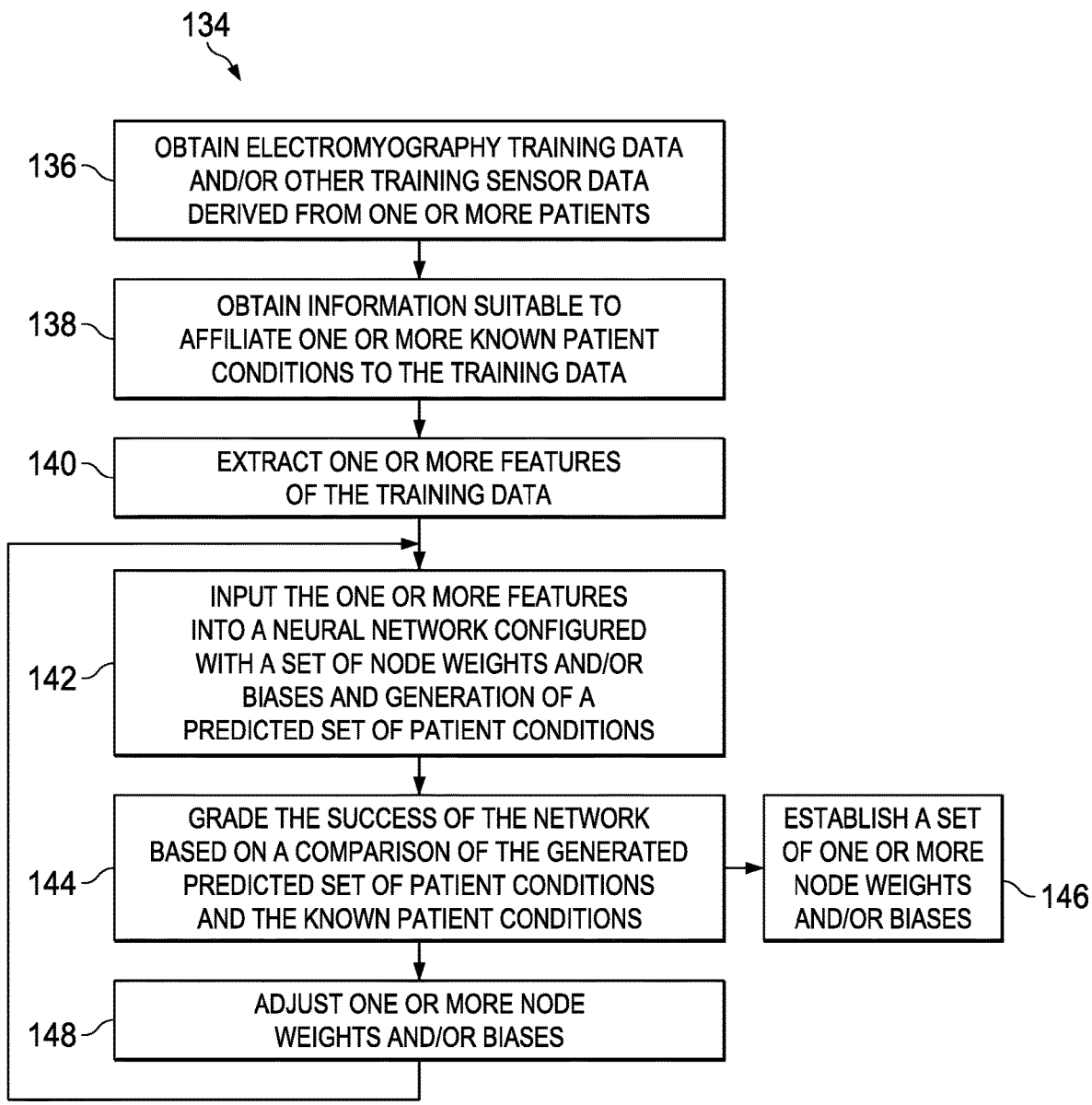
FIG. 12 shows embodiments of a method of training a neural network.

In some embodiments, methods of training a neural network are described. For example, some embodiments of a method 134 of training a neural network are shown in FIG. 12. In a step 136 of the method 134, training a neural network may include obtaining electromyography data and/or other sensor data derived from one or more patients. The electromyography data may be from raw or processed signal appropriately configured to define one or more feature values. In some embodiments, those feature values may later be applied to detect one or more patient conditions using a neural network as trained in methods herein such as the method 134. In some embodiments, raw electromyography signal from a patient may be collected. However, in some embodiments, other or additional information suitable to train a network may be obtained from a storage database including electromyography data. The stored data may include raw signal or may be compressed in some way yet still maintaining information associated with one or more feature values.

In a step 138, information may be obtained that is suitable to affiliate one or more patient conditions to the training data collected in step 136. For example, in some embodiments, for different parts of training data, one or more verified patient conditions, including, for example, whether seizure related signals are present, may be matched to training data or a part of the training data. Any of the verification methods and procedures described herein may be used to establish a condition affiliated with a patient. For example, in some embodiments, to verify a patient condition, electromyography data together with EEG data and video information may be reviewed by one or more persons specifically trained to identify and classify seizures. In some embodiments, as described, for example, in relation to FIG. 8 a physiological parameter that has not yet manifested at the time of collection of a part of training data may be affiliated with one or more part of training data.

In the step 140, training data may be processed to extract one or more feature values. As described above, in some embodiments, feature data itself may be stored in a storage database. Accordingly, in the step 140, feature data may be extracted from a raw or lesser processed signal and/or simply recorded or organized for further use as appropriate.

In the step 142, the one or more features extracted or organized as described herein may be input into a neural network. The neural network may include a set of node weights and/or biases. For example, in some embodiments, in a first time that step 142 is executed, node weights and/or biases may be randomly generated. In other embodiments, node weights and/or biases may be selected based on expected values that may be expected to be successful. Thus, for example, node weights and/or biases may begin training in a configuration that is most likely to efficiently lead to convergence between known and predicted conditions. Further in the step 142, a predicted set of patient conditions may be generated based on the currently used node weights and/or biases.

In the step 144, grading the success of the network based on a comparison of the generated predicted set of patient conditions and the known patient conditions may be executed. For example, in some embodiments, deviation values between known and predicted patient parameters may be determined.

In the step 148, one or more node weights and/or biases may be adjusted based on how well the predicted and known patient conditions correlate. As shown in FIG. 12, an adjusted set of node weights and/or biases may be determined and used to generate a next set of predicted patient conditions. Alternatively, as shown in the step 146, it may be established that a group of used node weights and/or biases sufficiently predicts or has converged to predict the known patient conditions affiliated with the training data.

Various devices in the apparatus of FIGS. 1-3 may communicate with each other via wired or wireless communication. The system 10 may comprise a client-server or other architecture and may allow communication via network 30. Of course, system 10 may comprise more than one server and/or client. In other embodiments, system 10 may comprise other types of network architecture, such as a peer-to-peer architecture, or any combination or hybrid thereof.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices may comprise one or more computers or programs that issue commands or requests for service provided by one or more other computers or programs, or servers. The various devices in FIG. 1, may be servers or clients depending on their function and configuration. Servers and/or clients may variously be or reside on, for example, mainframe computers, desktop computers, PDAs, smartphones (such as Apple's iPhone™, Motorola's Atrix™ 4G, Motorola's Droid™, Samsung's Galaxy S™, Samsung's Galaxy Note™, and Research In Motion's Blackberry™ devices), tablets (such as Sony's Xperia™, Samsung's Galaxy Tab™, and Amazon Kindle™) netbooks, portable computers, portable media players with network communication capabilities (such as Microsoft's Zune HD™ and Apple's iPod Touch™ devices), cameras with network communication capabilities, smartwatches, wearable computers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software or a combination thereof. A program may be created using any suitable programming language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video processors and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, and EEPROM. Memory may be virtualized and may be provided in or across one or more devices and/or geographic locations, such as RAID technology. An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless and may use multiplexers, network interface cards, modems, IDSN terminal adapters, line drivers, and the like. The network may comprise any suitable topology, such as point-to-point, bus, star, tree, mesh, ring, and any combination or hybrid thereof.

Wireless technology may take many forms such as person-to-person wireless, person-to-stationary receiving device, person-to-a-remote alerting device using one or more of the available wireless technologies such as ISM band devices, WiFi, Bluetooth, cell phone SMS, cellular (CDMA2000, WCDMA, etc.), WiMAX, WLAN, and the like.

Communication in and among computers, I/O devices, and network devices may be accomplished using a variety of protocols. Protocols may include, for example, signaling, error detection and correction, data formatting, and address mapping. For example, protocols may be provided according to the seven-layer Open Systems Interconnection model (OSI model) or the TCP/IP model.

Additional information related to the methods and apparatus described herein may be understood in connection with the example provided below.

Example 1

Figure 13:
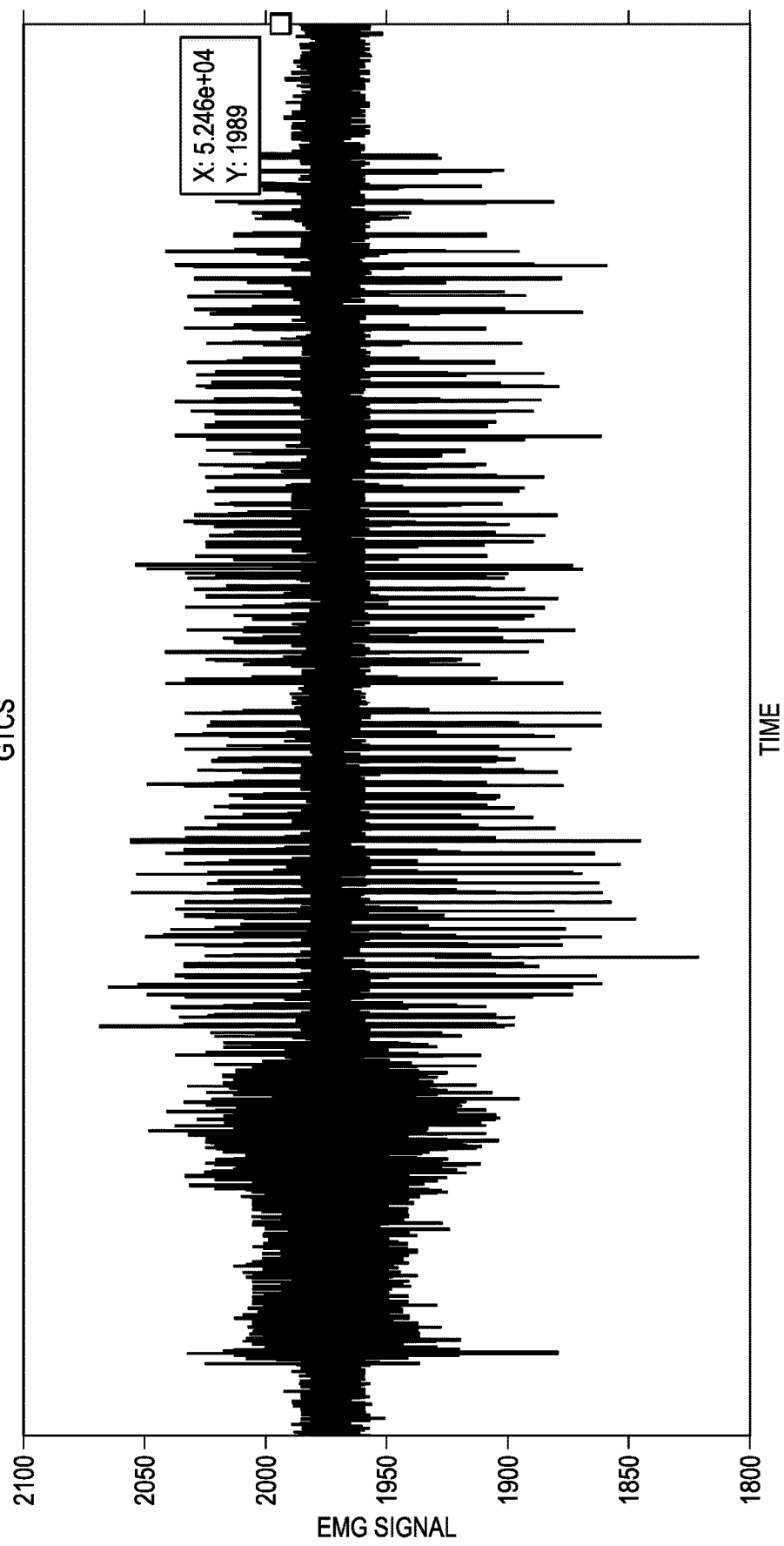
FIG. 13 shows electromyography data collected for a patient.

In this Example 1, patient EMG data was collected. For example, EMG data collected during a generalized tonic-clonic seizure for one patient in this Example 1 is shown in FIG. 13. Data was reviewed by persons trained to identify different types of seizure activity. In the data included herein, various parts of seizure activity were identified and paired with parts of the EMG data. Included among types of seizure or baseline activity identified herein and affiliated or paired with EMG data were pre-seizure, tonic, clonic, and post-ictal parts of data.

Figure 14:
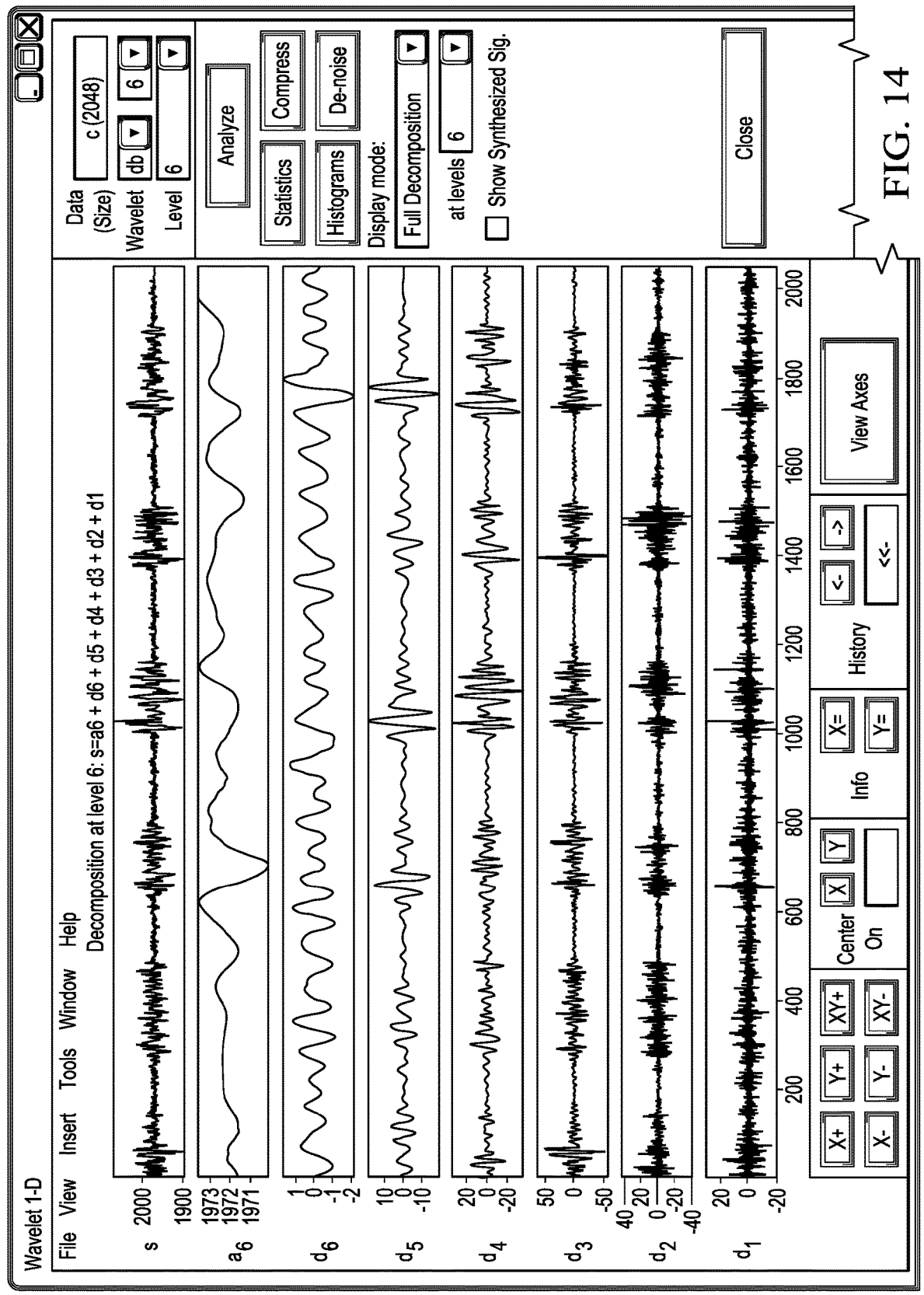
FIG. 14 shows electromyography data processed using wavelet analysis.
Figure 15:
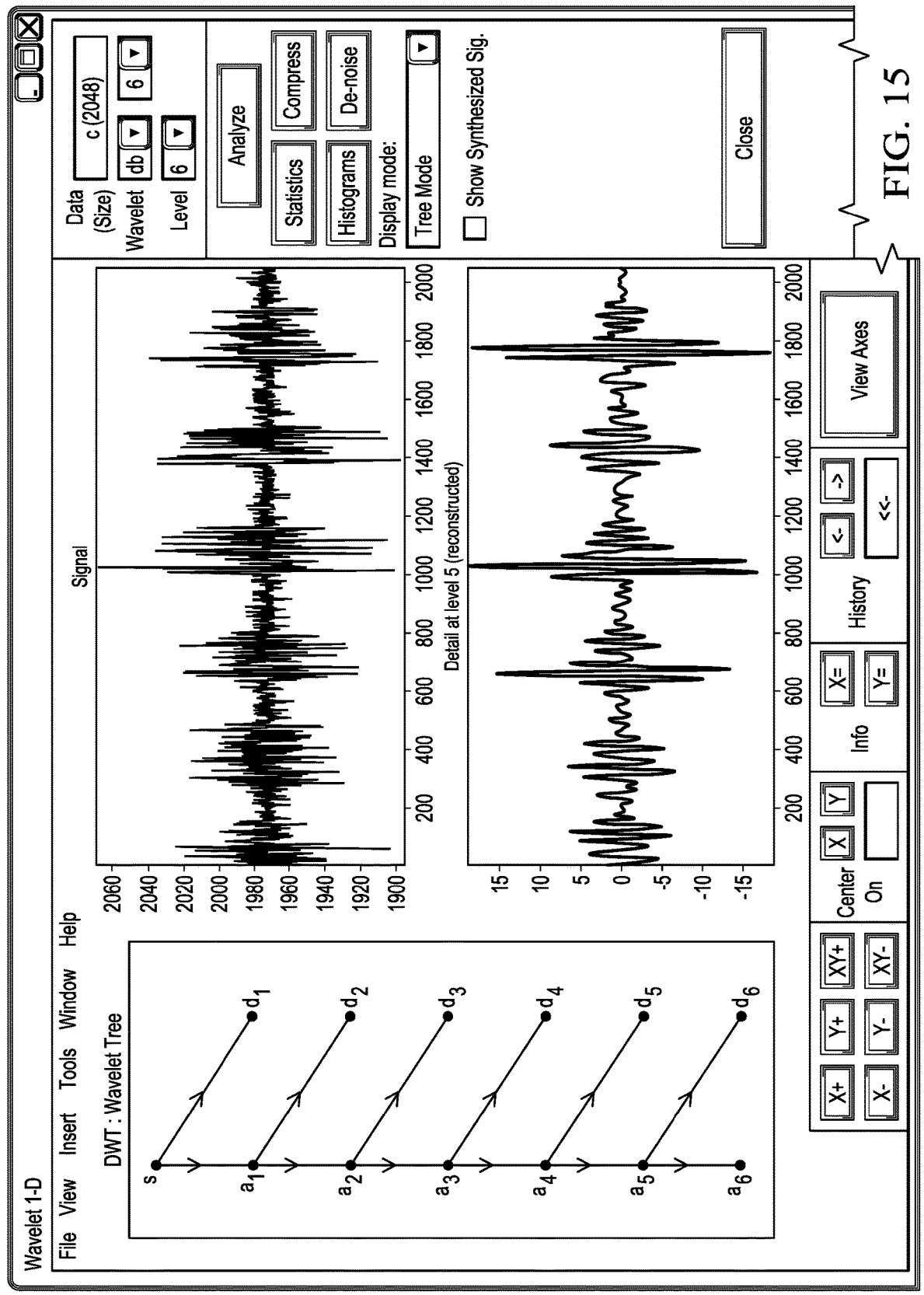
FIG. 15 shows additional electromyography data processed using wavelet analysis.

The EMG data was processed using wavelet analysis. In this Example 1, the analysis included processing according to Daubechies wavelet analysis. For example, the results of decomposition of clonic-phase portions of the data shown in FIG. 13 are shown in FIG. 14. In FIG. 14, data from various levels of decomposition of the signal are shown. Notably, a peak pattern of the clonic-phase data was detected with good signal-to-noise. For example, signal-to-noise for detection of a clonic-phase burst pattern was high in the details provided in the third through fifth levels of signal decomposition. FIG. 15 shows some of the data collected at the fifth level of signal decomposition and a reconstructed version of the EMG data.

Figure 16:
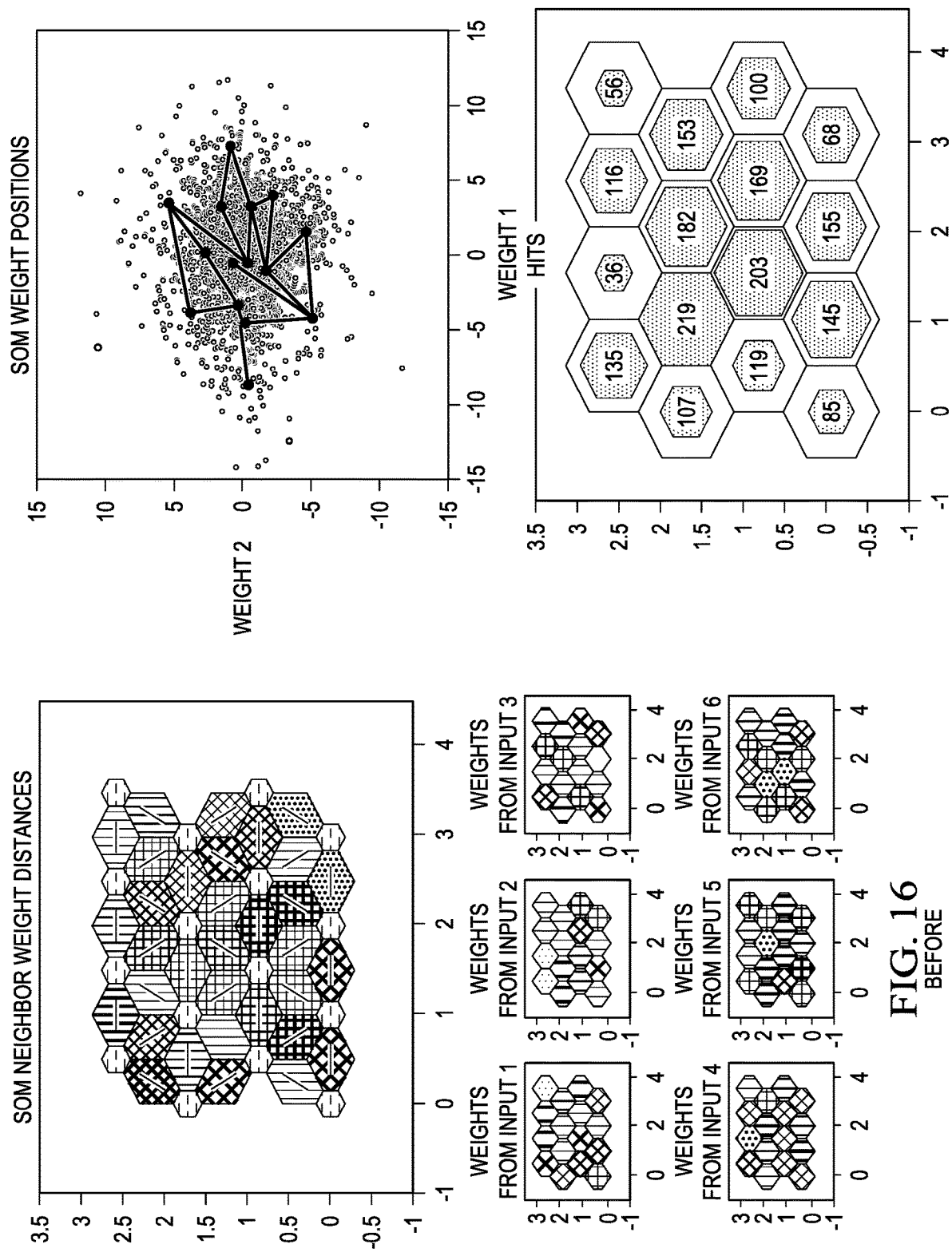
FIG. 16 shows processed electromyography data from a pre-seizure time period included in a self-organizing map.
Figure 17:
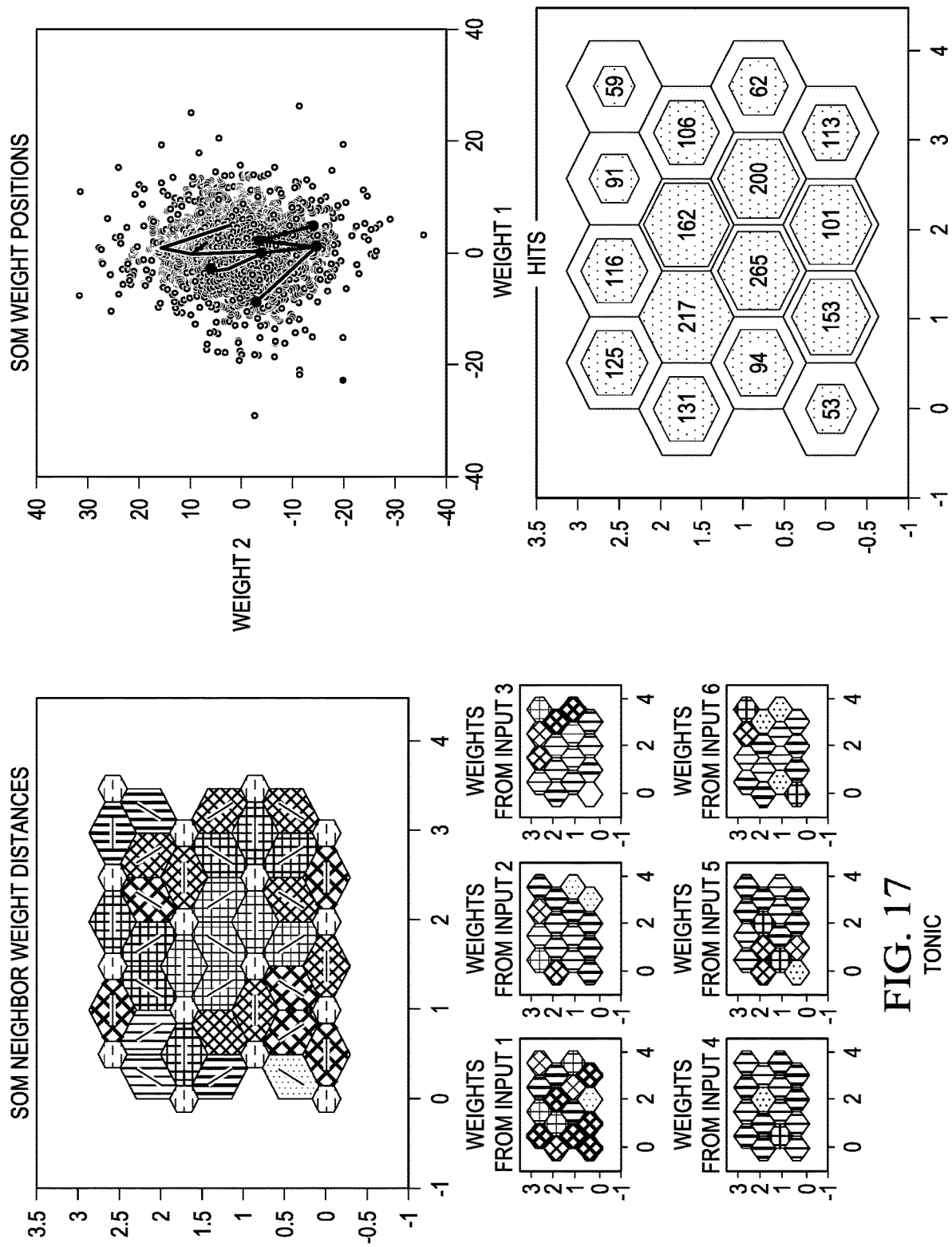
FIG. 17 shows processed electromyography data from a tonic phase time period included in a self-organizing map.
Figure 18:
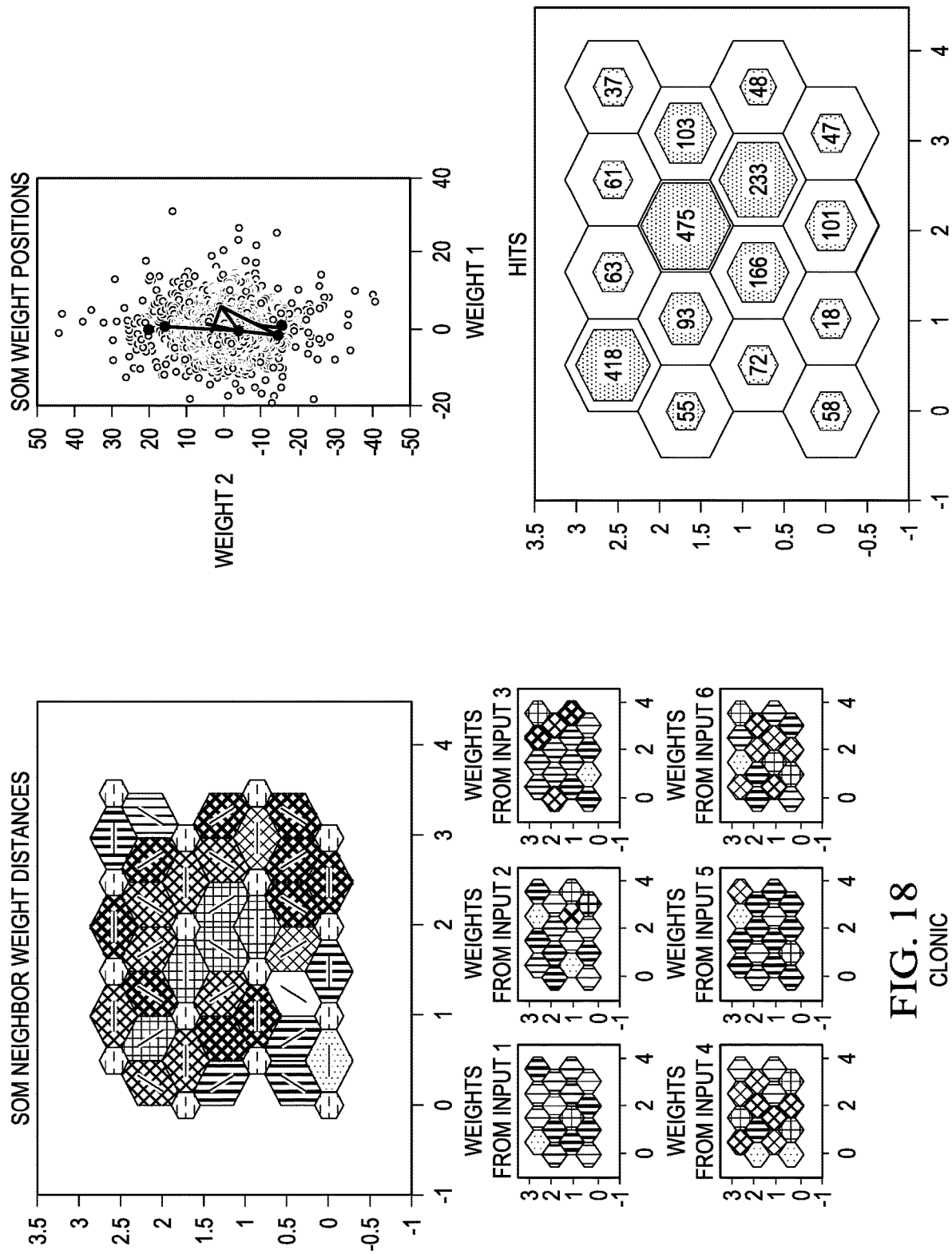
FIG. 18 shows processed electromyography data from a clonic phase time period included in a self-organizing map.
Figure 19:
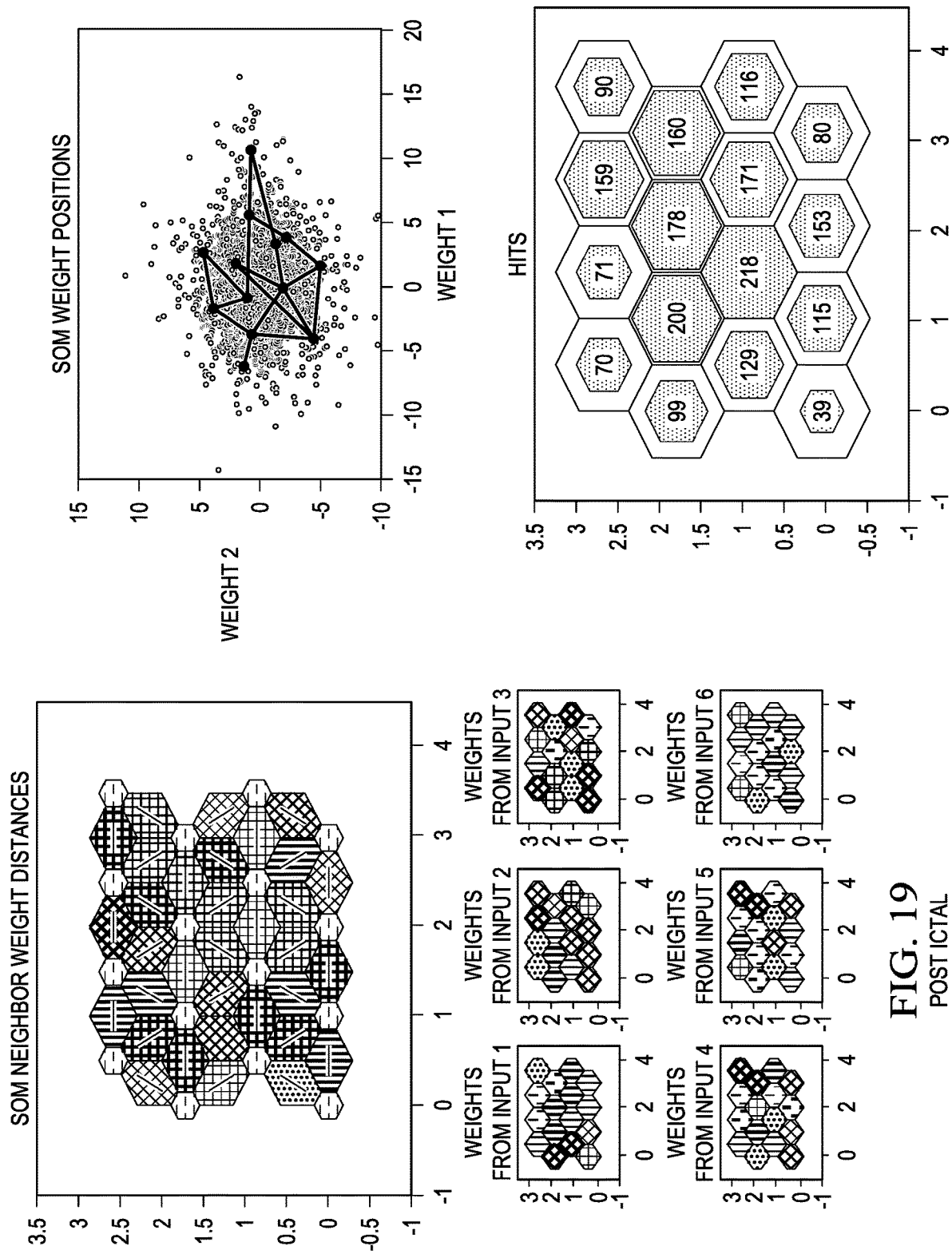
FIG. 19 shows processed electromyography data from a post-ictal time period included in a self-organizing map.
Figure 20:
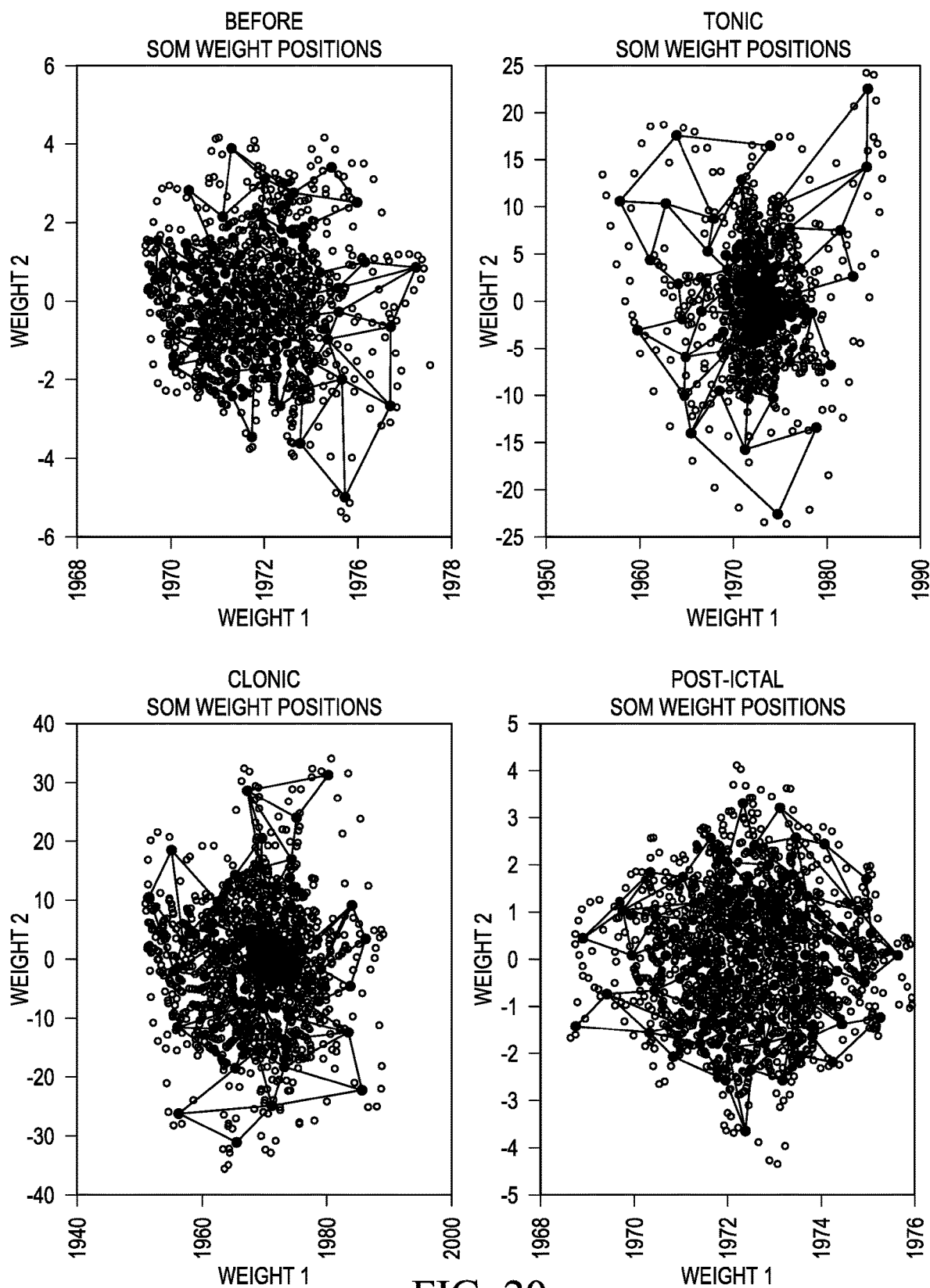
FIG. 20 shows self-organizing map data including electromyography data processed using wavelet analysis.

Approximation and details from the fifth level of signal decomposition were then further processed and input into a self-organizing-map (SOM), as displayed in FIGS. 16-20. FIG. 16 shows results obtained for periods of signal before a seizure. FIG. 17 shows results obtained during the tonic phase of a seizure. FIG. 18 shows results obtained during the clonic phase of a seizure. FIG. 19 shows results obtained during post-ictal periods. FIG. 20 shows additional results in the form of self-organizing-maps derived using Daubechies wavelet analysis.

Although the disclosed subject matter and its advantages have been described in detail, it should be understood that various changes, substitutions and alterations can be made herein without departing from the invention as defined by the appended claims. Moreover, the scope of the claimed subject matter is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

We claim:

1. A method of monitoring a patient for seizure activity comprising:
    monitoring a patient using one or more electromyography electrodes to obtain an electromyography signal during a monitoring period;
    processing with a processor said electromyography signal to determine values of one or more features of said electromyography signal;
    inputting said values of the one or more features of said electromyography signal into a neural network trained to identify an increased risk of central nervous system depression during recovery from a detected seizure;
    said neural network being trained to identify said increased risk of central nervous system depression during recovery from said seizure based on levels of oxygen saturation as measured during one or more training periods;
    processing said values of the one or more features of said electromyography signal using the neural network to determine one or more outputs of one or more output nodes of the neural network, wherein said one or more outputs include a first output indicating an increased risk of central nervous system depression during recovery from said seizure; and
    initiating a response based on said detected seizure.

2. The method of claim 1 wherein at least one output among the one or more outputs indicates an identification of clonic phase seizure activity.

3. The method of claim 1 wherein at least one output among the one or more outputs indicates an identification of tonic phase seizure activity.

4. The method of claim 1 wherein at least one output among the one or more outputs indicates detection of an electromyography signal pattern that is indicative of normal recovery from a seizure.

5. The method of claim 4 said neural network being trained to detect normal recovery from a seizure based on a correlation between said electromyography signal pattern and normal oxygen saturation level measured for one or more patients during the one or more training periods.

6. The method of claim 1 wherein at least one output among the one or more outputs is a prediction of a value of a physiological parameter that may be experienced by the patient following some time delay.

7. The method of claim 6 wherein said physiological parameter is oxygen saturation.

8. The method of claim 1 further comprising monitoring the patient using one or more saturated oxygen sensors during said monitoring period.

9. The method of claim 1 wherein said increased risk of central nervous system depression during recovery from said seizure is associated with a level of oxygen saturation of less than 80% to 90%.

10. The method of claim 1 wherein at least one output among the one or more outputs indicates an identification of a non-epileptic psychogenic seizure.

11. The method of claim 1 wherein said processing includes decomposition of the electromyography signal using a wavelet transform.

12. The method of claim 1 wherein said one or more of features of said electromyography signal are appropriate to identify changes in clonic-phase burst activity.

13. The method of claim 1 wherein said one or more of features of said electromyography signal include a clonic-phase burst repetition rate or clonic-phase burst amplitude.

14. An apparatus for monitoring a patient for seizure activity comprising:
    one or more electromyography electrodes configured to provide an electromyography signal of seizure-related muscle activity of a patient during a patient monitoring period;
    a processor configured to receive the electromyography signal and process the electromyography signal to determine values of one or more features of said electromyography signal;
    said processor further configured to input said values of the one or more features of said electromyography signal into a neural network trained to identify increased risk of central nervous system depression related to a detected seizure;
    said neural network being trained to identify said increased risk of central nervous system depression during recovery from said seizure based on levels of oxygen saturation as measured during one or more training periods;

said processor further configured to process said values of the one or more features of said electromyography signal using the neural network to determine one or more outputs of one or more output nodes of the neural network, wherein said one or more outputs include a first output indicating detection of an increased risk of central nervous system depression during recovery from said seizure; and said processor further configured to initiate a response based on said detected seizure.

15. The apparatus of claim 14 wherein at least one output among the one or more outputs indicates an identification of clonic phase seizure activity.

16. The apparatus of claim 14 wherein at least one output among the one or more outputs indicates identification of tonic phase seizure activity.

17. The apparatus of claim 14 further comprising a sensor suitable for measuring saturated oxygen levels for said patient.

18. The apparatus of claim 14 wherein at least one output among the one or more outputs indicates an identification of anon-epileptic psychogenic seizure.

19. The apparatus of claim 14 wherein said increased risk of central nervous system depression during recovery from said seizure is associated with a level of oxygen saturation of less than 80% to 90%.

20. The apparatus of claim 14 wherein at least one output among the one or more outputs indicates detection of an electromyography signal pattern that is indicative of normal recovery from a seizure.

* * * * *